United States Patent
Ning et al.

(10) Patent No.: US 12,357,258 B2
(45) Date of Patent: Jul. 15, 2025

(54) CALCIFICATION DETECTION SYSTEMS, METHODS AND APPARATUS IN CONE BEAM BREAST COMPUTED TOMOGRAPHY

(71) Applicant: KONING CORPORATION, Norcross, GA (US)

(72) Inventors: Ruola Ning, Atlanta, GA (US); Shaohua Liu, Atlanta, GA (US)

(73) Assignee: Koning Corporation, Norcross, GA (US)

(*) Notice: Subject to any disclaimer, the term of this patent is extended or adjusted under 35 U.S.C. 154(b) by 0 days.

(21) Appl. No.: 18/914,227

(22) Filed: Oct. 13, 2024

(65) Prior Publication Data

US 2025/0032077 A1    Jan. 30, 2025

Related U.S. Application Data

(63) Continuation of application No. PCT/US2023/018709, filed on Apr. 14, 2023.

(60) Provisional application No. 63/331,153, filed on Apr. 14, 2022, provisional application No. 63/401,475, filed on Aug. 26, 2022, provisional application No. 63/401,493, filed on Aug. 26, 2022, provisional application No. 63/401,513, filed on Aug. 26, 2022, provisional application No. 63/401,546, filed on Aug. 26, 2022, provisional application No. 63/401,548, filed on Aug. 26, 2022, provisional application No. 63/430,571, filed on Dec. 6, 2022, provisional application No. 63/459,250, filed on Apr. 13, 2023.

(51) Int. Cl.
*A61B 6/50* (2024.01)
*A61B 6/03* (2006.01)
*A61B 6/04* (2006.01)
*A61B 6/40* (2024.01)

(52) U.S. Cl.
CPC .............. *A61B 6/502* (2013.01); *A61B 6/032* (2013.01); *A61B 6/0435* (2013.01); *A61B 6/4085* (2013.01)

(58) Field of Classification Search
CPC ....... A61B 6/502; A61B 6/032; A61B 6/0435; A61B 6/4085
See application file for complete search history.

(56) References Cited

U.S. PATENT DOCUMENTS

| | | | |
|---|---|---|---|
| 6,987,831 B2 | 1/2006 | Ning | |
| 9,392,986 B2 | 7/2016 | Ning et al. | |
| 10,973,480 B2 | 4/2021 | Bailey et al. | |
| 11,364,003 B2 | 6/2022 | Boone et al. | |
| 2009/0080604 A1* | 3/2009 | Shores | A61B 6/487 378/37 |
| 2009/0232271 A1 | 9/2009 | Sendai | |
| 2010/0067648 A1 | 3/2010 | Kojima | |
| 2014/0037048 A1* | 2/2014 | Shores | A61B 6/482 378/19 |

(Continued)

*Primary Examiner* — Courtney D Thomas
(74) *Attorney, Agent, or Firm* — Bergman LLC; Michael Bergman

(57) ABSTRACT

A method of imaging a breast microcalcification feature by acquiring a tomographic imaging data set and a stationary imaging data set and combining the tomographic imaging data set with the stationary imaging data set to improve resolution and reduce blur in the resulting combined image. The resulting improve resolution image data set is evaluated for identification of breast calcifications for purposes of breast cancer screening, diagnosis and/or treatment.

20 Claims, 14 Drawing Sheets

(56) References Cited

U.S. PATENT DOCUMENTS

2014/0226783 A1 8/2014 Ning et al.
2019/0083051 A1 3/2019 Shimada et al.

\* cited by examiner

CALCIFICATION DETECTION SYSTEMS, METHODS AND APPARATUS IN CONE BEAM BREAST COMPUTED TOMOGRAPHY

CROSS-REFERENCE TO RELATED APPLICATIONS

The present application is a continuation of PCT patent application PCT/US2023/018709 filed on Apr. 14, 2023, which claims the benefit of provisional patent applications OMNIBUS DISCLOSURE, set forth in an application for Letters Patent of the United States already filed on Apr. 14, 2022 as U.S. Provisional Application No. 63/331,153, and FIXTURING AND SUPPORT FOR MEDICAL IMAGING, set forth in an application for Letters Patent of the United States already filed on Aug. 26, 2022 as U.S. Provisional Application No. 63/401,475, and ERGONOMIC IMPROVEMENTS IN CONE BEAM BREAST COMPUTED TOMOGRAPHY, set forth in an application for Letters Patent of the United States already filed on Aug. 26, 2022 as U.S. Provisional Application No. 63/401,493, and STATIONARY DETAIL IMAGING IN CONE BEAM BREAST COMPUTED TOMOGRAPHY, set forth in an application for Letters Patent of the United States already filed on Aug. 26, 2022 as U.S. Provisional Application No. 63/401,513, and CONE BEAM BREAST COMPUTED TOMOGRAPHY WITH PATIENT SUPPORT SUBSYSTEM, set forth in an application for Letters Patent of the United States already filed on Aug. 26, 2022 as U.S. Provisional Application No. 63/401,546, and, CONE BEAM BREAST COMPUTED TOMOGRAPHY WITH PIVOTAL GANTRY SUBSYSTEM, set forth in an application for Letters Patent of the United States already filed on Aug. 26, 2022 as U.S. Provisional Application No. 63/401,548, and ULTRASONIC HYBRID IMAGING IN CONE BEAM BREAST COMPUTED TOMOGRAPHY, set forth in an application for Letters Patent of the United States already filed on Dec. 6, 2022 as U.S. Provisional Application No. 63/430,571, and CALCIFICATION DETECTION SYSTEMS, METHODS AND APPARATUS IN CONE BEAM BREAST COMPUTED TOMOGRAPHY set forth in an application for Letters Patent of the United States already filed on Apr. 13, 2023 as U.S. Provisional Application No. 63/459,250, the disclosures of all of which are herewith incorporated by reference in their entireties.

FIELD OF THE INVENTION

The present invention relates to the field of cone beam tomographic imaging, and in particular to the field of calcification detection in tomographic imaging.

SUMMARY

According to the National Cancer Institute, one out of eight women will be diagnosed with breast cancer in her lifetime. And while a reduction in mortality from breast cancer is evident in published reports, each year 40,000 women will die of the disease.

The optimal breast imaging technique detects tumor masses when they are small, preferably less than 10 mm in diameter. It is reported that 93% of women with mammographically detected invasive breast carcinoma 1-10 mm have a 16-year survival rate. In addition, as the diameter of the tumor at detection decreases, the probability of metastasis declines sharply. If a breast tumor is detected when it is 10 mm or less, the probability of metastasis will be equal to 7.31%. If a 4 mm carcinoma is detected, the metastatic probability will be decreased by more than a factor of 10, to 0.617%.

Mammography, which on average can detect cancers about 12 mm in size, was the most effective tool for the early detection of breast cancer until the advent of cone beam breast computed tomography. Mammography has relatively low sensitivity to small breast cancers (under several millimeters). Specificity and the positive predictive value of mammography remain limited owing to structure and tissue overlap. The limited sensitivity and specificity in breast cancer detection of mammography are due to its poor contrast detectability, which is common for all types of projection imaging techniques (projection imaging can only have up to 10% contrast detectability), and mammography initially detects only 65-70% of breast cancers. The sensitivity of mammography is further reduced to as low as 30% in the dense breast. Digital mammography (DM) was developed to try to overcome the limitations inherent in screen-film mammography (SFM) by providing improved contrast resolution and digital image processing; however, a large-scale clinical trial, the Digital Mammographic Imaging Screening Trial (DMIST), showed that the rates of false positives for DM and SFM were the same.

The relatively low specificity of mammography leads to biopsy for indeterminate cases, despite the disadvantages of added cost and the stress it imposes on patients. Nearly 80% of the over one million breast biopsies performed annually in the U.S. to evaluate suspicious mammographic findings are benign, burdening patients with excessive anxiety and the healthcare system with tremendous cost. There is a need for more accurate characterization of breast lesions in order to reduce the biopsy rate and the false-positive rate of pre-biopsy mammograms.

To address the mammography limitations indicated above, one of the inventors has previously developed Cone Beam Breast Computed Tomography (CBBCT). Briefly, the major features of CBBCT include a horizontal, ergonomically designed patient table with a modular insert to optimize coverage of the uncompressed breast, including the chest wall; wide openings (1 m) on each side of the patient table for easy access to the breast for positioning and potentially good access for imaging-guided biopsy and other procedures without significantly changing the basic platform; and slip-ring technology that facilitates efficient dynamic contrast imaging studies and angiogenesis imaging in the future.

The results of phantom studies indicate that CBBCT can achieve a spatial resolution up to about 2.8 lp/mm, allowing detection of a 2 mm carcinoma and microcalcifications about 0.2 mm in size for an average size breast (about 13 cm in diameter at the chest wall) with a total dose of about 5 mGy. This dose is less than that of a single mammography exam, assuming two views are required for each breast. The image quality of CBBCT for visualizing breast tissues, breast tumors and calcifications is excellent, and coverage of the breast, including the chest wall region, is at least equivalent to mammography. Visualization of major blood vessels is very good without using a contrast agent.

Accordingly, CBBCT offers significant improvement in detecting and biopsying suspected lesions in a patient. Further, in many procedures using CBBCT, an image can be acquired without requiring the compression of the breast tissue universally associated with mammography. The compressive breast fixturing apparatus used in mammography is widely considered to be uncomfortable, and is often cited as a factor that discourages patients from seeking otherwise desirable breast cancer screenings. Additional improvements in CBBCT imaging offer the potential to expand on these benefits. In light of the foregoing, the ability to perform improved CBBCT imaging without resorting to the uncomfortable breast fixation associated with mammography is highly desirable.

One approach to further improving the detection of breast cancer is to make use of the association that exists between breast tissue calcifications and tumor prevalence.

Although the presence of calcification in breast tissue does not necessarily indicate malignancy, certain patterns of calcifications (such as type clusters with irregular shapes and fine appearance) are associated with malignancy and/or precancerous changes to breast tissue. In a screening mammography program, the rate of recall because of calcifications was 1.7% and of these, 19% resulted in a cancer diagnosis. In the digital mammography era, about one-sixth of all recalls are for calcifications. Up to 50% of breast cancers can be associated with calcification while 15-30% of calcifications biopsied for various reasons tend to be malignant in asymptomatic patients.

Calcifications are commonly associated with ductal carcinoma in situ (which is considered a stage 0 cancer). In addition, the presence of calcifications in one breast and not the other can be indicative of increased risk. As such, the ability to detect and characterize calcifications within the breast, on both screening and diagnostic bases, can be beneficial.

Breast calcifications tend to occur as macrocalcifications or microcalcifications. Macrocalcifications are not generally considered indicative of substantial cancer risk. Microcalcifications appear as fine white specks and certain patterns of microcalcifications are associated with an increased prevalence of cancerous tissue.

Breast calcification that are diagnostically significant include four classes of suspicious calcification morphology which are, in order of increasing concern: coarse heterogeneous (irregular, generally 0.5-1 mm); amorphous indistinct and/or small ("powdery", "cloud", or "cottony"), such that another specific shape cannot be determined; fine pleomorphic: variable shape ("shards of glass" or "crushed stone"), generally less than 0.5 mm; and fine linear or fine-linear branching: thin (<0.5 mm), linear, branching or irregularly arranged ("casting").

Also significant are calcification distribution (besides diffuse, which is almost always benign), which are listed here with in increasing order of concern:
1) regional: scattered in a larger volume (>2 cm in greatest linear dimension) of breast tissue and not in the expected ductal distribution;
2) grouped: a cluster of at least 5 calcifications within 1 cm from each other, in an area at most 2 cm in greatest linear dimension;
3) linear: calcifications arrayed in a line suggestive of deposition along ducts;
4) segmental: calcium deposits in ducts and branches of a segment or lobe.

Thus, for suspicious morphologies, a linear or segmental distribution more strongly increase the probability of malignancy than does a group. Although not an inherently suspicious morphology, punctate calcifications can be suspicious if they are new, increased, or linear or segmental in distribution.

To best take advantage of the characterizations developed above, the inventors have identified a need to improve CBBCT imaging so as to permit the resolution of calcifications down to 0.1 mm or less by in vitro imaging. The results of such an improvement will be highly significant in terms of both screening and diagnostic applications.

Consistently realizing image resolution down to 0.1 mm or less requires substantial advancements beyond existing CBBCT technology. After careful consideration, the present inventors have arrived at novel and advantageous developments and improvements well adapted to achieve previously unavailable imaging results. These results are improved through the application of improved imaging apparatus and methods, as well as methods and apparatus directed toward stabilization and timing of image acquisition events.

In one aspect, the inventors have identified motion artifacts intrinsic to existing equipment as a source of blurring in imaging. The ability to control and moderate the effects of these motions represent further opportunities for improved imaging, and the potential to achieve the resolution required for the effective identification of diagnostically significant regions of calcification.

In a further aspect, the inventors have identified the reduction of patient motion as an opportunity to improve resolution and reduce image blur. Patient motion originates, for example, with patient breathing, patient heartbeat, and various voluntary and involuntary motions of the patient musculature.

In light of these identified opportunities, the inventors have conceived, and here reduced to practice, technical improvements bringing the desired calcification imaging within reach.

For example, in certain embodiments of the invention, the continuous rotational motion of a structural gantry supporting previously available CBBCT imaging apparatus is replaced by a plurality of discrete motions. Accordingly, where CBBCT exposures are taken with earlier imaging apparatus in motion, in contrast, a system according to principles of the present invention captures images while the imaging apparatus is substantially stationary with respect to a stabilized breast. The result is that motion-induced image blur is reduced or eliminated and effective image resolution is improved.

Thus, for example, a CBBCT image according to principles of the invention is acquired as a plurality of individual exposures with the gantry substantially stopped at, for example, 2° intervals of rotation. One of skill in the art will appreciate that, in certain embodiments of the invention, images will be taken at intervals of rotation between 0° and 0.5°, at intervals between 0.5° and 1°, at intervals between 1° and 2°, at intervals between 2° and 4°, at intervals between 4° and 10°, or any combination thereof deemed to be beneficial in a particular application.

In other embodiments of the invention a subject breast is immobilized, and during a first time interval within the period of immobilization, a conventional moving CBBCT image is acquired.

During a different time interval within the period of immobilization, one or more stationary images are acquired. The stationary images are acquired with the imaging apparatus substantially static with respect to the stabilized breast.

The stationary images are relatively few, as compared with the CBBCT image data set. For example, 1, 2, 5, 10, 20 or, 30 stationary images might be acquired in an exemplary procedure or system as compared to e.g., 200, 300 or 400 CBBCT image-pulse exposures. The data representing the stationary images are then numerically combined with the data of the CBBCT image to provide a CBBCT image of increased effective resolution.

In certain embodiments of the invention, the stationary images are substantially evenly distributed around the periphery of the breast, at regular or irregular rotational intervals of, for example and without limitation, 5°, 10°, 20°, 30°, etc. In other embodiments of the invention, stationary images are concentrated within a limited subsection of the rotational arc of the CBBCT image, where the limited subsection of the rotational arc will, in certain instances, be selected to correspond to a particular region of interest within the breast tissue identified for enhanced examination and/or characterization.

In certain embodiments of the invention, the CBBCT image will be captured using a relatively high energy x-ray signal from the x-ray source. In certain embodiments of the invention, the stationary image will be captured using a relatively low energy x-ray signal from the x-ray source.

In certain embodiments of the invention, the CBBCT image will be captured using an x-ray source having a focal point diameter (or having its focal point diameter parameter set to) approximately 0.3 mm.

In certain embodiments of the invention, a stationary image will be captured using an x-ray source having a focal point diameter (or having its focal point diameter parameter set to) approximately 0.1 mm.

In certain embodiments of the invention, the combination of CBBCT and stationary images is accomplished using deep learning AI algorithms to enhance regions of calcification.

In certain embodiments of the invention, in order to reduce image acquisition time, and therefore minimize the opportunity for subject tissue motion, a CBBCT image, as referenced above is performed over a rotational interval of 180° plus detector width, rather than a default 360° plus detector width.

In certain embodiments of the invention, in order to reduce image blurring due to imaging apparatus motion, and therefore improve effective resolution, a CBBCT image, as referenced above is performed over a longer time interval. Thus, for example a 360° gantry rotation will, in certain embodiments of the invention, be executed over a time interval of for example 30 seconds rather than, for example 10 seconds. In other embodiments of the invention, for example, a 180° gantry rotation will, be executed over a time interval of for example 30 seconds rather than, for example 10 seconds.

As suggested above, and further described below, in certain embodiments of the invention, the initial step of immobilizing the breast to be imaged will be beneficial, and is implied.

In current practice, a patient undergoing CBBCT lies prone on a table. A subject breast is disposed downward through an aperture in an upper surface of the table, depending from the chest wall into an imaging chamber disposed under the table. The position of the breast within the imaging chamber is maintained by stasis of the patient (i.e., keeping the patient stationary) as the patient lies on an upper surface of the table.

An imaging apparatus is coupled to a mobile gantry which is supported on a bearing device for rotation about an axis of rotation. The axis of rotation is disposed in a generally vertical orientation and passes through the aperture in the upper surface of the table. Preferably, an approximate centroid of the breast to be imaged is arranged such that the axis of rotation passes through the approximate centroid.

During imaging, the mobile gantry rotates around the axis of rotation, bringing the imaging apparatus through at least a portion of a circular path. As it traverses this path, the imaging apparatus emits a series of x-ray pulses and captures corresponding image data which is processed to prepare a tomographic model of the breast.

To avoid blurring during individual x-ray pulses, and to maintain consistency of images between the pulses, the patient remains stationary during imaging. Even small variations in spatial positioning of the breast can result in reduced image clarity.

In existing CBBCT systems, the breast hangs freely within the imaging chamber. In order to provide the stability required to improve breast imaging for calcification detection, certain embodiments of the invention include a breast support apparatus. In certain embodiments, the breast support apparatus includes a stabilizer unit and a positioning apparatus coupled to the stabilizer unit so as to provide adjustable positioning of the stabilizer unit with respect to a reference frame of the tomographic imager.

In certain embodiments, the stabilizer unit includes a generally rigid body having a primary surface region configured to be disposed in contact with a corresponding surface region of a subject breast. In selected embodiments, the generally rigid body includes a material selected for a desirable level of transparency with respect to an operative wavelength of imaging energy. Accordingly, in certain embodiments, the generally rigid body includes one or more of expanded polystyrene; polystyrene; polyethylene; Acrylonitrile Butadiene Styrene (ABS); polypropylene; acrylics (e.g., polymethyl methacrylate); polyamide; polyaramid; aerogels; ceramics; fiber reinforced composites; and polycarbonate (e.g., Lexan©), among others.

The following description is provided to enable any person skilled in the art to make and use the disclosed inventions and sets forth the best modes presently contemplated by the inventors of carrying out their inventions. In the following description, for purposes of explanation, numerous specific details are set forth in order to provide a thorough understanding of the present invention. It will be apparent to one skilled in the art, however, that the present invention may be practiced without these specific details. In other instances, well-known structures and devices are shown in block diagram form in order to avoid unnecessarily obscuring the substance disclosed. These and other advantages and features of the invention will be more readily understood in relation to the following detailed description of the invention, which is provided in conjunction with the accompanying drawings.

It should be noted that, while the various figures show respective aspects of the invention, no one figure is intended to show the entire invention. Rather, the figures together illustrate the invention in its various aspects and principles. As such, it should not be presumed that any particular figure is exclusively related to a discrete aspect or species of the invention. To the contrary, one of skill in the art will appreciate that the figures taken together reflect various aspects and embodiments exemplifying the invention.

Correspondingly, reference throughout the specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout the specification are not necessarily all referring to the same embodiment. Furthermore, the particular features, structures, or characteristics may be combined in any suitable manner in one or more embodiments.

DETAILED DESCRIPTION

Figure 1:
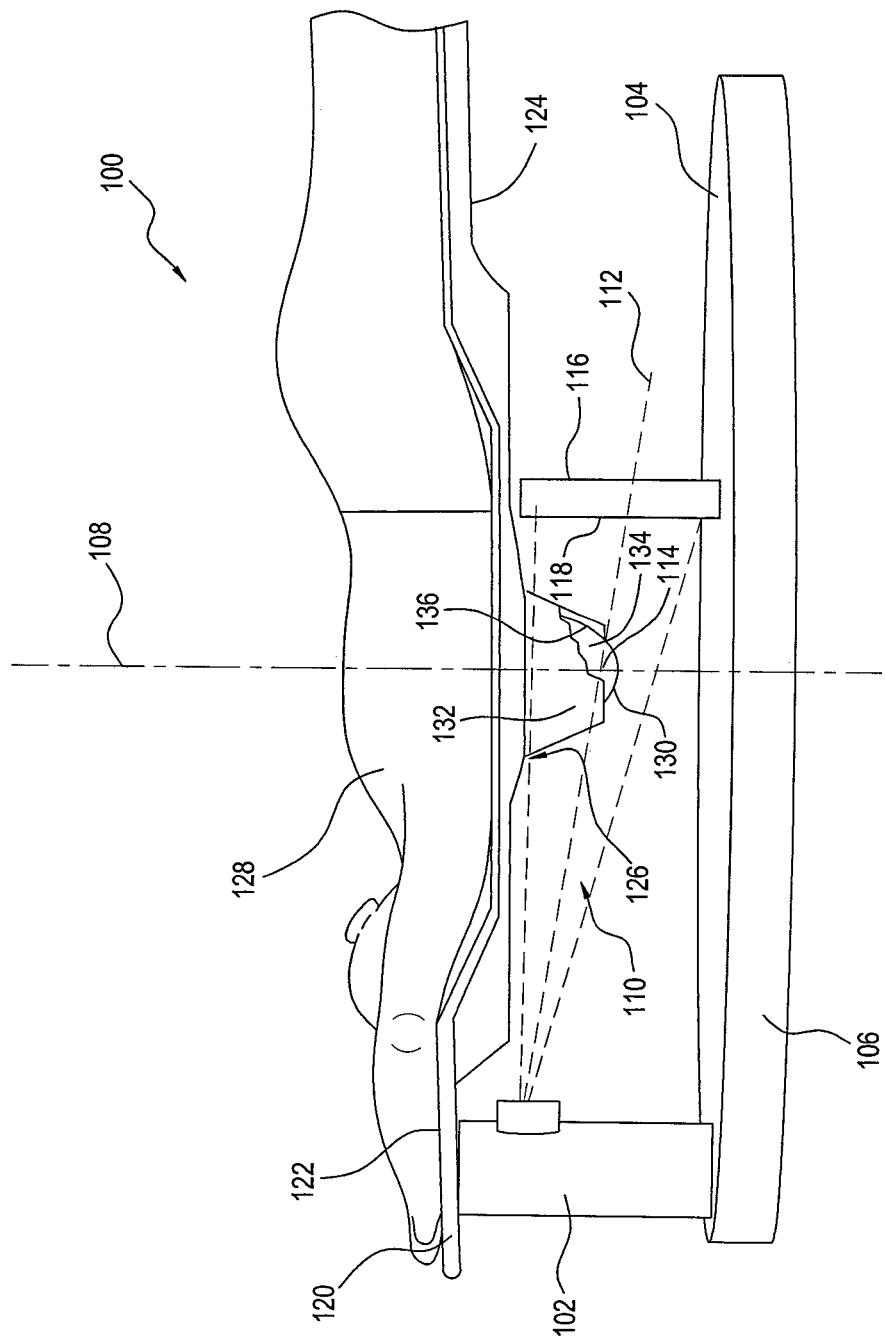
FIG. 1 shows in schematic cutaway perspective view a portion of a CBBCT breast imaging system including an exemplary breast stabilizer unit.

FIG. 1 shows, in cutaway perspective view, a portion of an exemplary CBBCT imaging system 100 including a breast support apparatus, prepared according to principles of the invention. The system 100 includes an x-ray source 102. The x-ray source 102 is mounted on an upper surface 104 of a rotary gantry 106. The rotary gantry 106 is supported by a bearing, and arranged for rotation about an axis of rotation 108.

The x-ray source 102 is configured to emit a beam of x-rays 110. The beam of x-rays 110 defines a beam longitudinal axis 112 that, in the illustrated embodiment, intersects (at 114) the axis of rotation 108.

In certain embodiments of the invention, beam 110 is configured as a cone beam. In certain configurations, a cross-section of the beam 110 taken transverse to the longitudinal axis 112 defines a disk of substantially uniform x-ray intensity with a substantially circular perimeter.

In other configurations within the scope of the invention, a cross-section of the beam 110 taken transverse to the longitudinal axis 112 defines a region of substantially uniform x-ray intensity with a substantially circular perimeter save for a portion of the disc outwardly of a chord of said circular perimeter. As will be appreciated on consideration of the further disclosure below, in certain embodiments, the chord will be disposed in generally parallel spaced relation to a lower surface of a patient table.

In still further configurations within the scope of the invention, a cross-section of the beam 110 taken transverse to the longitudinal axis 112 defines a region of substantially uniform x-ray intensity with a polygonal perimeter, where the polygonal perimeter will, in respective embodiments and configurations, include any of a triangular perimeter, a square perimeter, a pentagonal perimeter, a hexagonal perimeter, a perimeter of any higher geometric shape, and/or a perimeter having any arbitrary curve or combination of line segments and curves according to the demands of a particular application. Moreover, it will be appreciated that any of the cross-sectional configurations described above may define a beam having a nonuniform intensity including, without limitation an intensity that falls to zero in certain regions of the cross-section.

An x-ray detector 116 is also mounted on the upper surface 104 of the rotary gantry 106. In one exemplary embodiment, the x-ray detector 116 includes a flat panel detector having a generally planar receiving surface 118. Receiving surface 118 is disposed generally transverse to longitudinal axis 112 and on the opposite side of axis of rotation 108 from the x-ray source 102.

Rotation of the gantry 106 about axis of rotation 108 during operation of the imaging system 100 will result in the receiving surface 118 following a transit path about axis of rotation 108. In a typical configuration, the transit path will include at least a portion of a circle disposed transverse to, and centered at, axis of rotation 108. It should be noted, however, that other transit paths (however achieved) are considered to be within the scope of the invention, and to be disclosed herewith.

In certain embodiments of the invention, one or both of the x-ray source 102 and the x-ray detector 116 are arranged so that their respective positions on the upper surface 104 of gantry 106 are adjustable. For example, the x-ray source 102 and the x-ray detector 116 may be adjustable in a radial direction with respect to axis of rotation 108, in a circumferential direction with respect to axis of rotation 108, in a direction towards or away from gantry surface 104, or in any other orientation or manner deemed beneficial by the designer or user of a particular apparatus embodying the invention. One of skill in the art will appreciate that by appropriate configuration of the x-ray being cross-section and positioning of the x-ray source and/or x-ray detector, the entirety of a subject breast and/or various regions of the breast will be preferentially imaged.

A patient table 120, otherwise known as a patient interface panel, includes an upper surface 122 and a lower surface 124. An aperture 126 communicates between the upper surface 122 and lower surface 124 of the table. The upper surface 122 is arranged to support a patient 128, typically with the patient lying prone on upper surface 122, as illustrated. In this arrangement, a breast 130 of the patient is disposed pendant from the patient's chest wall downwardly through aperture 126.

In the illustrated embodiment, a breast stabilizer unit 132 (shown in cutaway view) is disposed at aperture 126, and extending below lower surface 124. At least a portion of an external surface region 134 of breast 130 is disposed in contact with an internal circumferential surface region 136 of stabilizer unit 132.

As noted above, and as will be further discussed below, the effectiveness of calcification detection correlates to increased image resolution and decreased blurring, among other factors. After careful consideration, the present inventors have concluded that image resolution can be improved, and blurring reduced, by a combination of improved x-ray source apparatus and methods, improved detector apparatus and methods, the reduction of motion artifacts through improved mechanical systems, and appropriate signal processing. Accordingly, disclosed herewith are novel combinations of methods and apparatus embodying these desirable improvements in characteristics, certain aspects of which are reflected in the system overview presented in FIG. 2 below.

Figure 2:
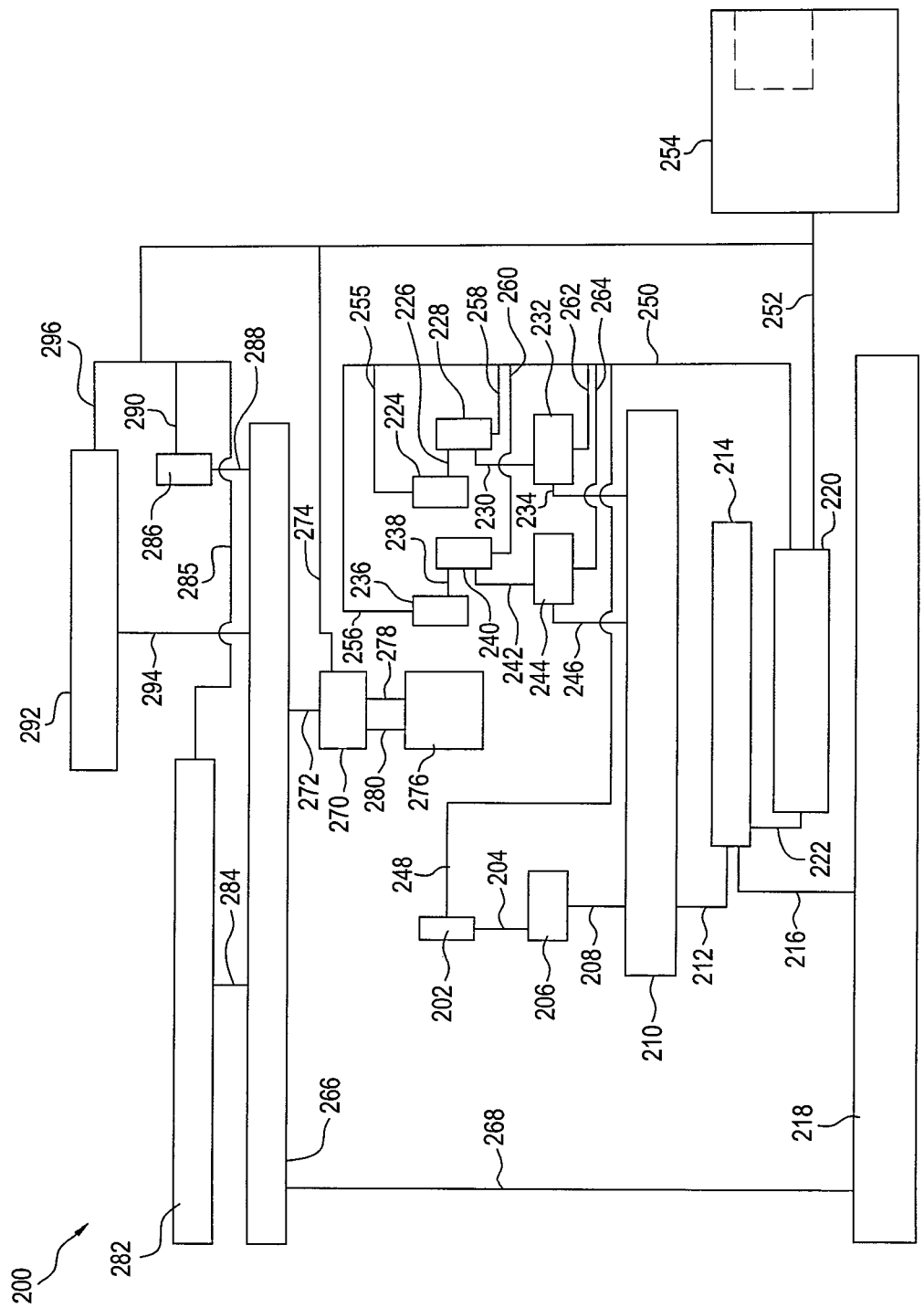
FIG. 2 shows in block diagram form the structural and signaling relationship of certain aspects of an exemplary CBBCT breast imaging system including calcification detection features prepared according to principles of the invention.

FIG. 2 illustrates, in schematic block diagram form, a portion of a CBBCT imaging system 200 including improved calcification detection features prepared according to principles of the invention. The system 200 includes an x-ray source 202. The x-ray source 202 is mechanically coupled 204 to a positioning system 206. The positioning system 206 is, in turn, mechanically coupled 208 to a rotary gantry 210.

Rotary gantry 210 is operatively mechanically coupled 212 to a rotary bearing 214 for rotational support about an axis of rotation. The rotary bearing 214 is, in turn, mechanically coupled 216 to a structural base element 218.

In certain embodiments of the invention, a slip ring 220 is mechanically coupled 222 across the rotary bearing 214 for conveying measurement and control and imaging data and signals onto and off of the rotary gantry 210.

In some embodiments of the CBBCT imaging system, a flat panel x-ray detector 224 is mechanically coupled 226 to a vertical positioning actuator 228. The vertical positioning actuator 228 is mechanically coupled 230 to a radial positioning actuator 232 which is, in turn, mechanically coupled 234 to the rotary gantry 210.

Accordingly, the vertical 228 and radial 232 positioning actuators are respectively coupled to the flat panel detector 224 and the rotary gantry 210. It will be appreciated by one of skill in the art, however, that the opposite order of coupling will be employed in other embodiments of the invention and, any of a wide variety of mechanisms and arrangements will be employed for positioning of the flat panel detector 224 with respect to the rotary gantry 210 in respective embodiments of the invention.

In an exemplary embodiment of the invention, as shown, a photon counting x-ray detector 236 is mechanically coupled 238 to a vertical positioning actuator 240. The vertical positioning actuator 240 is mechanically coupled 242 to a radial positioning actuator 244 which is, in turn, mechanically coupled 246 to the rotary gantry 210. As discussed above in relation to the flat panel detector, any of a wide variety of mechanisms and arrangements will be employed for positioning of the photon counting detector 236 with respect to the rotary gantry 210 in respective embodiments of the invention.

In certain embodiments of the invention, the x-ray source 202 is signalingly coupled 248 through a communications channel 250 through the slip ring 220 and a further communications channel 252 to a controller 254 such as, for example, a digital computer. This signaling coupling is, in certain embodiments of the invention, operative to provide power, data signals such as, e.g. operational parameters, feedback signals, and other useful signals unidirectionally and/or bidirectionally between the x-ray source 202 and the controller 254.

In respective embodiments of the invention, the signaling coupling and/or communication channel hardware, e.g., 248, 250, 252 will include, for example and without limitation, electrical wiring, optical fiber, flexible printed circuit devices, various waveguides for electromagnetic communications of any desirable wavelength, including digital, analog and mixed signal. In addition, the desired communications will be achieved, in certain embodiments, through free air signals such as for example, electromagnetic signals, acoustic signals, or other signals that are known or may become known in the art.

In certain embodiments of the invention, the flat panel detector 224 is signalingly coupled 255 through the communications channel 250, through the slip ring 220 and through the further communications channel 252 to the controller 254. This signaling coupling is, in certain embodiments of the invention, operative to provide power, data signals such as, e.g. operational parameters, feedback signals, and other useful signals unidirectionally and/or bidirectionally between the flat panel detector 224 and the controller 254.

In certain embodiments of the invention, the photon counting detector 236 is signalingly coupled 256 through the communications channel 250 through the slip ring 220 and the further communications channel 252 to the controller 254. This signaling coupling is, in certain embodiments of the invention, operative to provide power, data signals such as, e.g. operational parameters, feedback signals, and other useful signals unidirectionally and/or bidirectionally between the photon counting detector 236 and the controller 254.

Similarly, in certain embodiments of the invention, the vertical positioning actuators 228 and 240 are respectively signalingly coupled 258, 260 through the communications channel 250 through the slip ring 220 and the further communications channel 252 to the controller 254. This signaling coupling is, in certain embodiments of the invention, operative to provide power, data signals such as, e.g. operational parameters, feedback signals, and other useful signals unidirectionally and/or bidirectionally between the vertical positioning actuators 228, 240 and the controller 254.

In certain embodiments of the invention, the horizontal positioning actuators 232 and 244 are respectively signalingly coupled 262, 264 through the communications channel 250 through the slip ring 220 and the further communications channel 252 to the controller 254. This signaling coupling is, in certain embodiments of the invention, operative to provide power, data signals such as, e.g. operational parameters, feedback signals, and other useful signals unidirectionally and/or bidirectionally between the horizontal positioning actuators 232, 244 and the controller 254.

In certain embodiments of the invention, servos and operational controls will be effected through the communications channels described above. In other embodiments of the invention, local servo loops and/or feedback arrangements (such as, e.g., digital servo loops, analog servo loops, and phase locked loops) will provide immediate control of the apparatus, while parametric/setpoint signaling will be communicated from the controller 254 where appropriate. Naturally, combinations of the foregoing schemes and other appropriate schemes (e.g., open-loop control schemes) will be employed where consistent with the needs of a particular embodiment or application of the invention.

As shown in the exemplary embodiment of FIG. 2, imaging system 200 includes a patient support panel 266. Patient support panel 266 is mechanically coupled 268 to the structural base element 218. In certain embodiments, the patient support panel 266 will include an aperture for receiving a patient breast therethrough.

According to the illustrated exemplary embodiment, a receiver 270 is mechanically coupled 272 to the patient support panel 266. In certain embodiments of the invention, the receiver 270 is signalingly coupled 274 through the further communications channel 252, to the controller 254. This signaling coupling is, in certain embodiments of the invention, operative to provide power, data signals such as, e.g. operational parameters, feedback signals, biometric signals, and other useful signals unidirectionally and/or bidirectionally between the receiver 270 and the controller 254.

A breast stabilizer unit 276 is configured and adapted to be removably mechanically coupled 278 to the receiver 270 for support. In certain embodiments of the invention, the breast stabilizer unit 276, when in operation, is signalingly coupled 280 to the receiver 270, and through the receiver 270, via signaling coupling 274 through the further communications channel 252 to the controller 254. One of skill in the art will appreciate that this signal coupling will operate to provide power, data signals such as, e.g. operational parameters, feedback signals, biometric signals, and other useful signals unidirectionally and/or bidirectionally between the breast stabilizer unit 276 and the controller 254.

As illustrated, the CBBCT imaging system 200 optionally includes a patient positioning support 282. As shown, in certain embodiments of the invention, the patient positioning support 282 will be mechanically coupled to 284, and/or supported by the patient interface panel 266. In exemplary embodiments, the patient positioning support 282 will be configured as a mattress, a cushion, a fender, or any other apparatus effective to position the patient for effective operation of the imaging system 200 while reducing or optimizing patient motion and maintaining an optimum degree of patient comfort.

In certain embodiments of the invention, the patient positioning support 282 will be a reconfigurable apparatus that allows adjustment or other customization according to the physical and other characteristics of a patient, and the requirements of a particular process or procedure. In still further embodiments of the invention, the patient positioning support 282 will be an active apparatus that allows adjustment or other customization according to the physical and other characteristics of a patient, and the requirements of a particular process or procedure, automatically and/or without manual intervention by a clinician or technician.

In certain embodiments of the invention, the patient positioning support 282 is signalingly coupled 285 through the further communications channel 252 to the controller 254. This signaling coupling is, in certain embodiments of the invention, operative to provide power, data signals such as, e.g. operational parameters, feedback signals, and other useful signals unidirectionally and/or bidirectionally between the patient positioning support 282 and the controller 254.

In certain embodiments of the invention, the signaling coupling between the patient positioning support 282 in the controller 254 allows automatic and/or dynamic control of patient positioning by the controller 254.

As illustrated, the CBBCT imaging system 200 optionally includes a patient handgrip 286. As shown, in certain embodiments of the invention, the patient handgrip 286 is mechanically coupled to 288, and/or supported by the patient interface panel 266. In exemplary embodiments, the patient handgrip 286 will be configured for grasping by the patient to facilitate effective operation of the imaging system 200 while reducing or eliminating patient motion and maintaining an optimum degree of patient comfort.

In certain embodiments of the invention, the patient handgrip 286 will be a reconfigurable apparatus that allows adjustment or other customization according to the physical and other characteristics of a patient, and the requirements of a particular process or procedure. In still further embodiments of the invention, the patient handgrip 286 will be an active apparatus that allows adjustment or other customization according to the physical and other characteristics of a patient, and the requirements of a particular process or procedure automatically and/or without manual intervention by a clinician or technician.

In certain embodiments of the invention, the patient handgrip 286 is signalingly coupled 290 through the further communications channel 252 to the controller 254. This signaling coupling is, in certain embodiments of the invention, operative to provide power, data signals such as, e.g. operational parameters, feedback signals, biometric signals, and other useful signals unidirectionally and/or bidirectionally between the patient handgrip 286 and the controller 254.

In certain embodiments of the invention, the signaling coupling between the patient handgrip 286 and the controller 254 allows automatic and/or dynamic control of patient positioning by the controller 254. In further embodiments of the invention, the signaling coupling between the patient handgrip 286 and the controller 254 allows sensing of a patient condition such as, e.g., heart rate and timing during operation of the imaging system 200. It should be noted that in certain aspects of the invention, image acquisition will be synchronized to heart rate to minimize image blurring due to internal corporeal vibrations associated with and/or resulting from the heartbeat.

As illustrated, the CBBCT imaging system 200 optionally includes a patient back support element 292. As shown, in certain embodiments of the invention, the patient back support element 292 is mechanically coupled to 294, and/or supported by, the patient interface panel 266. In an alternative embodiment of the invention, the patient back support element 292 is mechanically coupled to, and/or supported by, the structural base element 218.

In certain embodiments of the invention, the patient back support element 292 will be a reconfigurable apparatus that allows adjustment or other customization according to the physical and other characteristics of a patient, and the requirements of a particular process or procedure. In still further embodiments of the invention, the patient back support element 292 will be an active apparatus that allows adjustment or other customization according to the physical and other characteristics of a patient, and the requirements of a particular process or procedure automatically and/or without manual intervention by a clinician or technician. In exemplary embodiments, the patient back support element 292 will include a bladder or expandable cushion that when activated, serves to urge the patient towards the patient interface panel 266. According to certain aspects of the invention, the patient back support element is effective to position the patient for effective operation of the imaging system 200 while reducing or eliminating patient motion and maintaining an optimum degree of patient comfort.

In certain embodiments of the invention, the patient back support element 292 is signalingly coupled 296 through the further communications channel 252 to the controller 254. This signaling coupling is, in certain embodiments of the invention, operative to provide power, data signals such as, e.g., operational parameters, feedback signals, biometric signals, and other useful signals unidirectionally and/or bidirectionally between the back support element 292 and the controller 254.

In certain embodiments of the invention, the signaling coupling between the back support element 292 and the controller 254 allows automatic and/or dynamic control of patient positioning by the controller 254. In further embodiments of the invention, the signaling coupling between the back support element 292 and the controller 254 allows sensing of a patient condition such as, e.g., heart rate and timing during operation of the imaging system 200. It should be noted that in certain aspects of the invention, image acquisition will be synchronized to heart rate to minimize image blurring due to internal corporeal vibrations associated with and/or resulting from the heartbeat.

Figure 3:
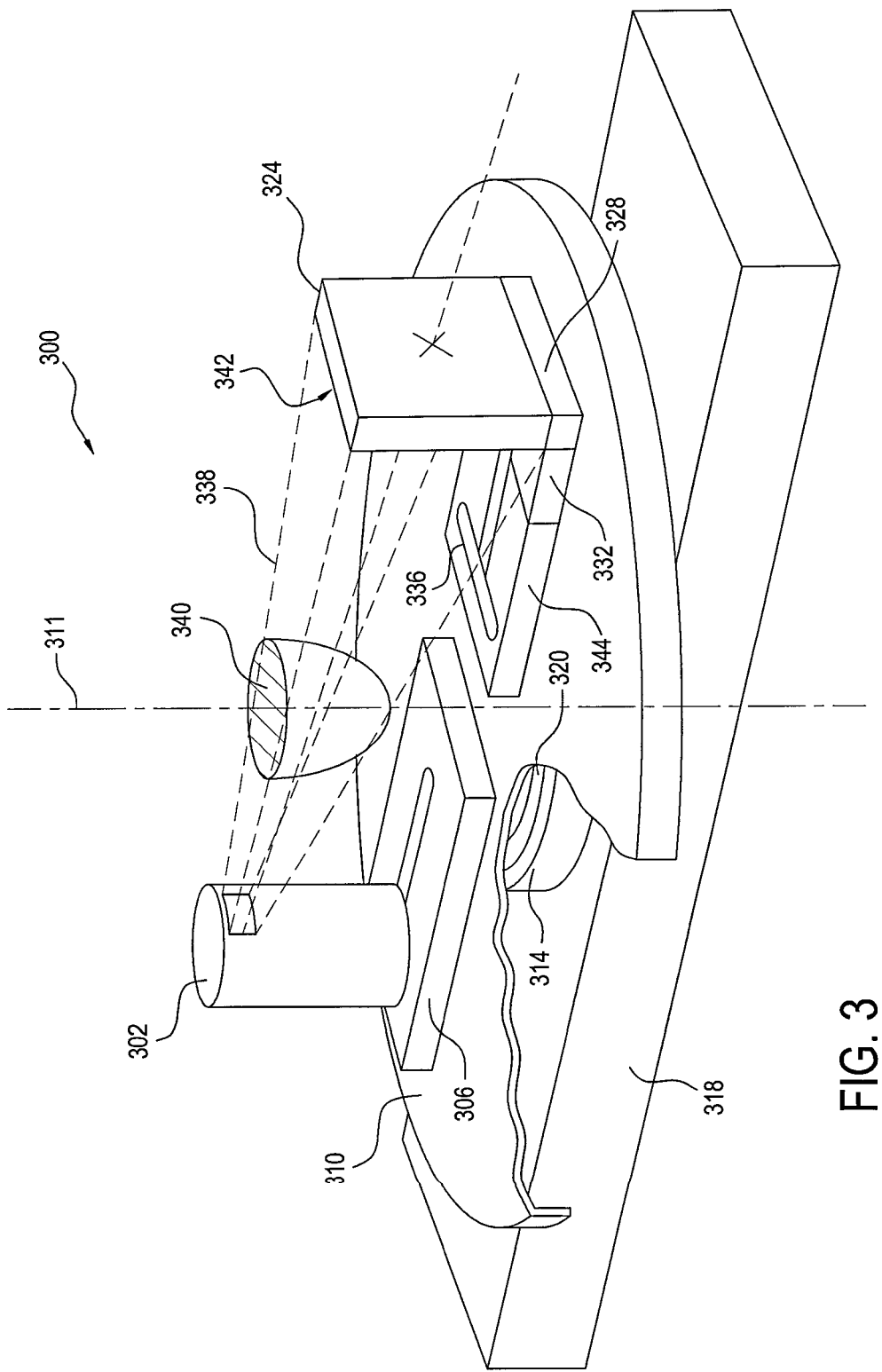
FIG. 3 shows in schematic cutaway perspective view, certain aspects of an exemplary CBBCT breast imaging system including calcification detection features in a first configuration according to principles of the invention.

FIG. 3 illustrates, in schematic cutaway perspective view, a portion of a CBBCT imaging system 300 including improved calcification detection features prepared according to principles of the invention. The system 300 includes an x-ray source 302. The x-ray source 302 is mechanically coupled to a positioning system 306. The positioning system 306 is, in turn, mechanically coupled to a rotary gantry 310.

Rotary gantry 310 is operatively mechanically coupled to a rotary bearing 314 for rotational support about an axis of rotation 311. The rotary bearing 314 is, in turn, mechanically coupled to a structural base element 318.

In certain embodiments of the invention, a slip ring 320 is mechanically coupled across the rotary bearing 314 for conveying measurement and control and biometric and imaging signals and data onto and off of the rotary gantry 310.

In some embodiments of the CBBCT imaging system, a flat panel x-ray detector 324 is mechanically coupled to a vertical positioning actuator 328. The vertical positioning actuator 328 is mechanically coupled to a radial positioning actuator 332 which is, in turn, mechanically coupled to the rotary gantry 310.

Accordingly, the vertical 328 and radial 332 positioning actuators are respectively coupled to the flat panel detector 324 and the rotary gantry 310. It will be appreciated by one of skill in the art that the opposite order of coupling will be employed in other embodiments of the invention and, any of a wide variety of mechanisms and arrangements will be employed for positioning of the flat panel detector 324 with respect to the rotary gantry 310 in respective embodiments of the invention.

In an exemplary embodiment of the invention, as shown, a photon counting x-ray detector 336 is mechanically coupled to a vertical positioning actuator (not visible). The vertical positioning actuator is mechanically coupled to a radial positioning actuator 344 which is, in turn, mechanically coupled to the rotary gantry 310. As discussed above in relation to the flat panel detector, any of a wide variety of mechanisms and arrangements will be employed for positioning of the photon counting detector 336 with respect to the rotary gantry 310 in respective embodiments of the invention.

It should be noted that, in FIG. 3, photon counting detector 336 is shown in a storage configuration, such that the photon counting detector 336 is disposed outside of, and does not interfere with, an x-ray beam 338, when emitted by the x-ray source 302. One of skill in the art will readily appreciate that operation of the vertical positioning actuator referenced above, as well as the radial positioning actuator 344 will cause translation of the photon counting detector 336 out of the illustrated storage configuration and into an operative configuration, as illustrated, for example, in FIG. 4 below.

When the photon counting detector 336 is disposed in the illustrated storage configuration, the x-ray beam 338 emitted by the x-ray source 302 is able to traverse a patient breast 340, disposed within imaging system 300 for imaging, and impinge on an imaging surface 342 of flat panel detector 324.

In certain embodiments of the invention, the x-ray source 302 is signalingly coupled through a communications channel through the slip ring 320 and a further communications channel to a controller such as, for example, a digital computer. This signaling coupling is, in certain embodiments of the invention, operative to provide power, data signals such as, e.g., operational parameters, feedback signals, and other useful signals unidirectionally and/or bidirectionally between the x-ray source 302 and the controller.

In respective embodiments of the invention, the signaling coupling and/or communication channel hardware will include, for example and without limitation, electrical wiring, optical fiber, flexible printed circuit devices, various waveguides for electromagnetic communications of any desirable wavelength, including digital, analog and mixed signal. In addition, the desired communications will be achieved, in certain embodiments, through free air signals such as for example, electromagnetic signals, acoustic signals, or other signals that are known or may become known in the art.

In certain embodiments of the invention, the flat panel detector 324 is signalingly coupled through the communications channel, through the slip ring 320 and through the further communications channel to the controller. This signaling coupling is, in certain embodiments of the invention, operative to provide power, data signals such as, e.g., operational parameters, feedback signals, and other useful signals unidirectionally and/or bidirectionally between the flat panel detector 324 and the controller.

In certain embodiments of the invention, the photon counting detector 336 is signalingly coupled through the communications channel through the slip ring 320 and the further communications channel to the controller. This signaling coupling is, in certain embodiments of the invention, operative to provide power, data signals such as, e.g., operational parameters, feedback signals, and other useful signals unidirectionally and/or bidirectionally between the photon counting detector 336 and the controller.

Similarly, in certain embodiments of the invention, the vertical positioning actuators e.g., 328 are respectively signalingly coupled, through the communications channel, through the slip ring 320 and the further communications channel, to the controller. This signaling coupling is, in certain embodiments of the invention, operative to provide power, data signals such as, e.g., operational parameters, feedback signals, and other useful signals unidirectionally and/or bidirectionally between the vertical positioning actuators, e.g., 328 and the controller.

In certain embodiments of the invention, the horizontal positioning actuators 332 and 344 are respectively signalingly coupled through the communications channel through the slip ring 320 and the further communications channel to the controller. This signaling coupling is, in certain embodiments of the invention, operative to provide power, data signals such as, e.g., operational parameters, feedback signals, and other useful signals unidirectionally and/or bidirectionally between the horizontal positioning actuators 332, 344 and the controller.

In certain embodiments of the invention, servos and operational controls will be effected through the communications channels described above. In other embodiments of the invention, local servo loops and/or feedback arrangements (such as, e.g., digital servo loops, analog servo loops, and phase locked loops) will provide immediate control of the apparatus, while parametric/setpoint signaling will be communicated from the controller where appropriate. Naturally, combinations of foregoing schemes and other appropriate schemes (including open loop control) will be employed where consistent with the needs of a particular embodiment or application of the invention.

Figure 4:
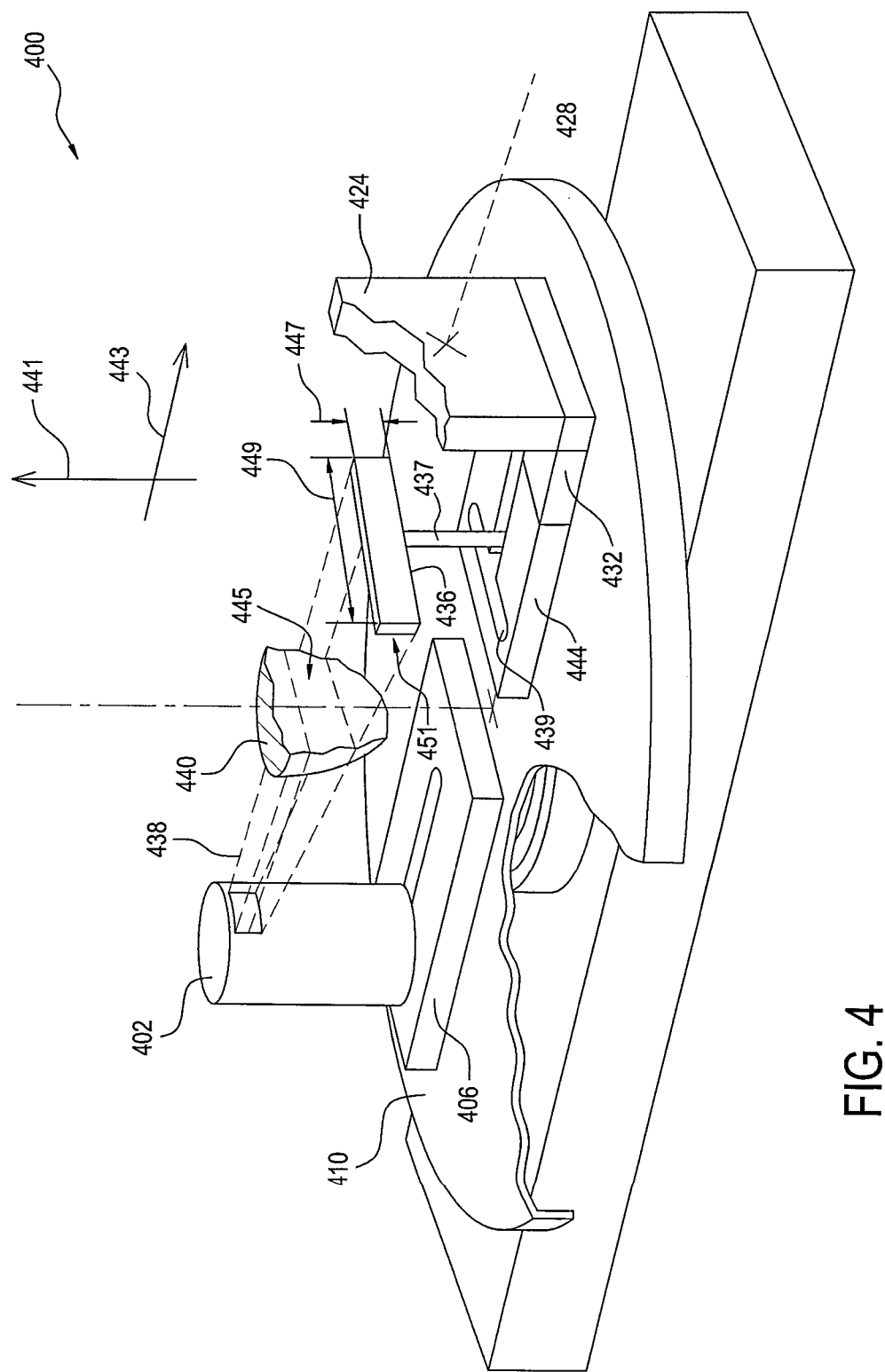
FIG. 4 shows in schematic cutaway perspective view, certain aspects of an exemplary CBBCT breast imaging system including calcification detection features in a second configuration according to principles of the invention.

FIG. 4 shows, in schematic cutaway perspective view, a portion of a CBBCT imaging system 400 having features similar to those of imaging system 300. Among other evident features, the imaging system 400 includes an x-ray source 402 mechanically coupled to a positioning system 406. The positioning system 406 is supported by a rotary gantry 410.

A flat-panel x-ray detector 424 is mechanically coupled to a vertical positioning actuator 428 which is mechanically coupled to a radial positioning actuator 432 which is, in turn, mechanically coupled to the rotary gantry 410. A photon counting detector 436 is mechanically coupled to a vertical actuator 437 which is, in turn, mechanically coupled to a radial actuator 444. Radial actuator 444 is mechanically coupled to the rotary gantry 410.

As noted above, photon counting detector 336 is disposed in a storage configuration. In contrast photon counting detector 436 is shown in an operative configuration. As will be evident to the reader, the photon counting detector 436 has been translated out of a storage recess 439 into the operative configuration by a vertical motion 441 of the vertical actuator 437, and by a radial motion 443 of the horizontal actuator 444. Consequently, photon counting detector 436 is positioned to effectively receive an x-ray beam 438 produced by the x-ray source 402.

In certain embodiments of the invention, the x-ray beam 438 is configured, e.g., by passing it through a shielding collimator, to have a cross-section with respective vertical and horizontal dimensions and positioning such that it primarily illuminates a region of interest 445 within a breast 440 being imaged. Preferably, respective vertical 447 and horizontal 449 dimensions of an imaging region 451 of the photon counting detector 436 correspond to the dimensions of the collimated x-ray beam as it arrives at the imaging region 451.

Accordingly, by coordinated operation of the shielding collimator and the vertical 437 and horizontal 444 actuators, a desired region of interest 445 of breast 440 can be effectively imaged. As will be further discussed below, in certain embodiments of the invention a tomographic image data set will be acquired by operation of the flat-panel detector 424, and one or more static images will be acquired by operation of the photon counting detector 436 to provide additional detail with respect to the region of interest 445. In certain embodiments of the invention, the tomographic image data and static image data will be processed to produce a tomographic image having improved resolution and/or reduced blur. These improvements, in turn, assist in the identification and characterization of calcification regions within the breast 440.

It will be appreciated by one of skill in the art that, in various embodiments, an imaging system prepared according to principles of the invention will acquire static images using the same flat-panel detector 424 as employed to acquire the tomographic images. In certain embodiments, the photon counting detector 436 will thus be omitted.

In other embodiments of the invention, a photon counting detector having dimensions sufficient to image the entirety of a subject breast 440 will be used, for example, in place of the flat-panel detector 424. Further, in certain embodiments of the invention, both the flat-panel detector 424 and the photon counting detector 436 will have dimensions sufficient to image the entire breast at once. In such an embodiment, the x-ray beam may nevertheless be collimated to image one or more desired regions of interest, thereby acquiring tomographic and/or static images of the subject breast 440. These images will, in certain embodiments, be combined or otherwise hybridized with otherwise acquired tomographic images of the breast 440 to produce improved screening and/or diagnostic and/or treatment results.

More generally, either X-ray detector can be any of a wide variety of two dimensional detectors including a flat panel detector, a two dimensional photon counting detector, two dimensional curved detector. To optimize the coverage of breast tissue at chest wall and the patient comfort, the top edge (dead space) of the detector should be minimal (as small as possible). To reduce motion artifacts and improve the sharpness of the reconstruction images, the frame rate of the detector should be at least 20 frames/second and at least 512×512 per frame. To obtain an isotropic high spatial resolution of the breast CT system, the cell size of the two dimensional detector should be equal to or smaller than 0.5 mm×0.5 mm/cell.

The apparatus of the cone beam breast CT acquires two-dimensional projection data. Acquisition geometries can be a single circle geometry, double circle geometry (for a large size of breast), a circle-plus-line geometry, half-circle-plus cone angle geometry, spiral cone beam geometry. One or more of these geometries are then employed to construct CBBCT 3D images from the 2D projection data. The reconstruction methods can be filtered backprojection, iterative algorithms, and/or AI deep learning algorithms. The specialized imaging processors can be used to perform the fast reconstruction and imaging processing.

Figure 5A:
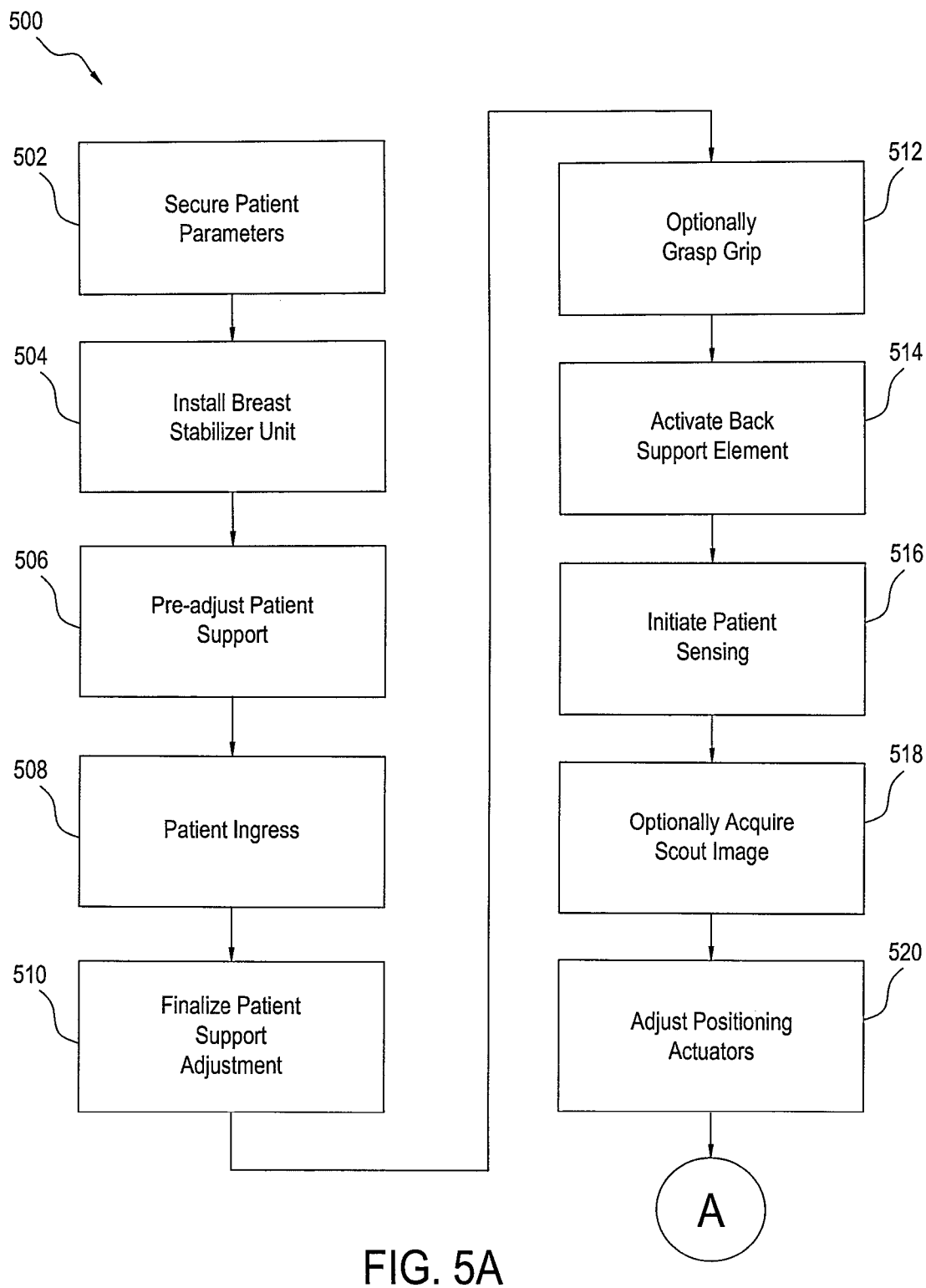
FIG. 5A shows in schematic block diagram form, certain aspects of a system and method for CBBCT imaging, including the imaging of breast calcification features.
Figure 5B:
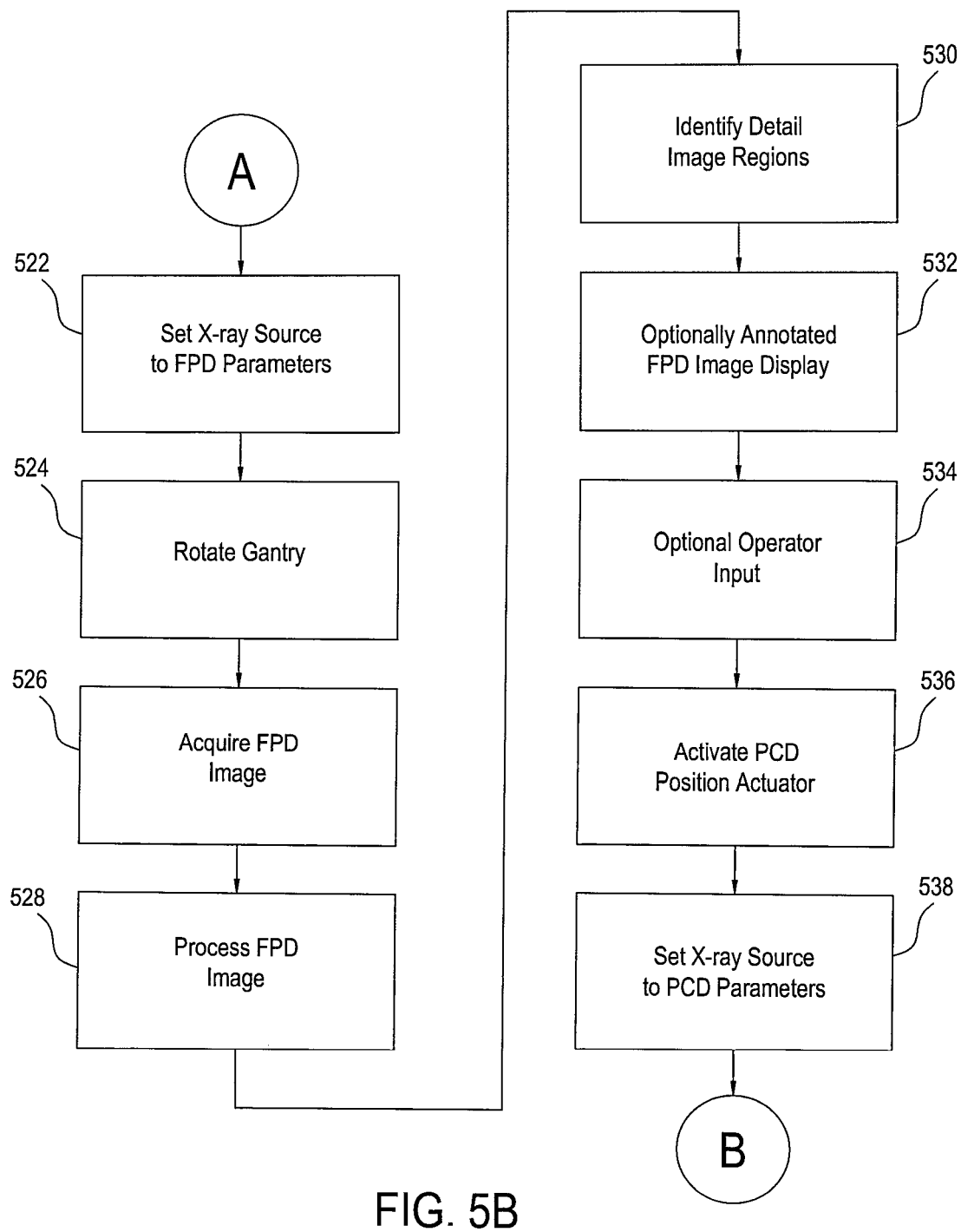
FIG. 5B shows in schematic block diagram form, further aspects of a system and method for CBBCT imaging, including the imaging of breast calcification features.
Figure 5C:
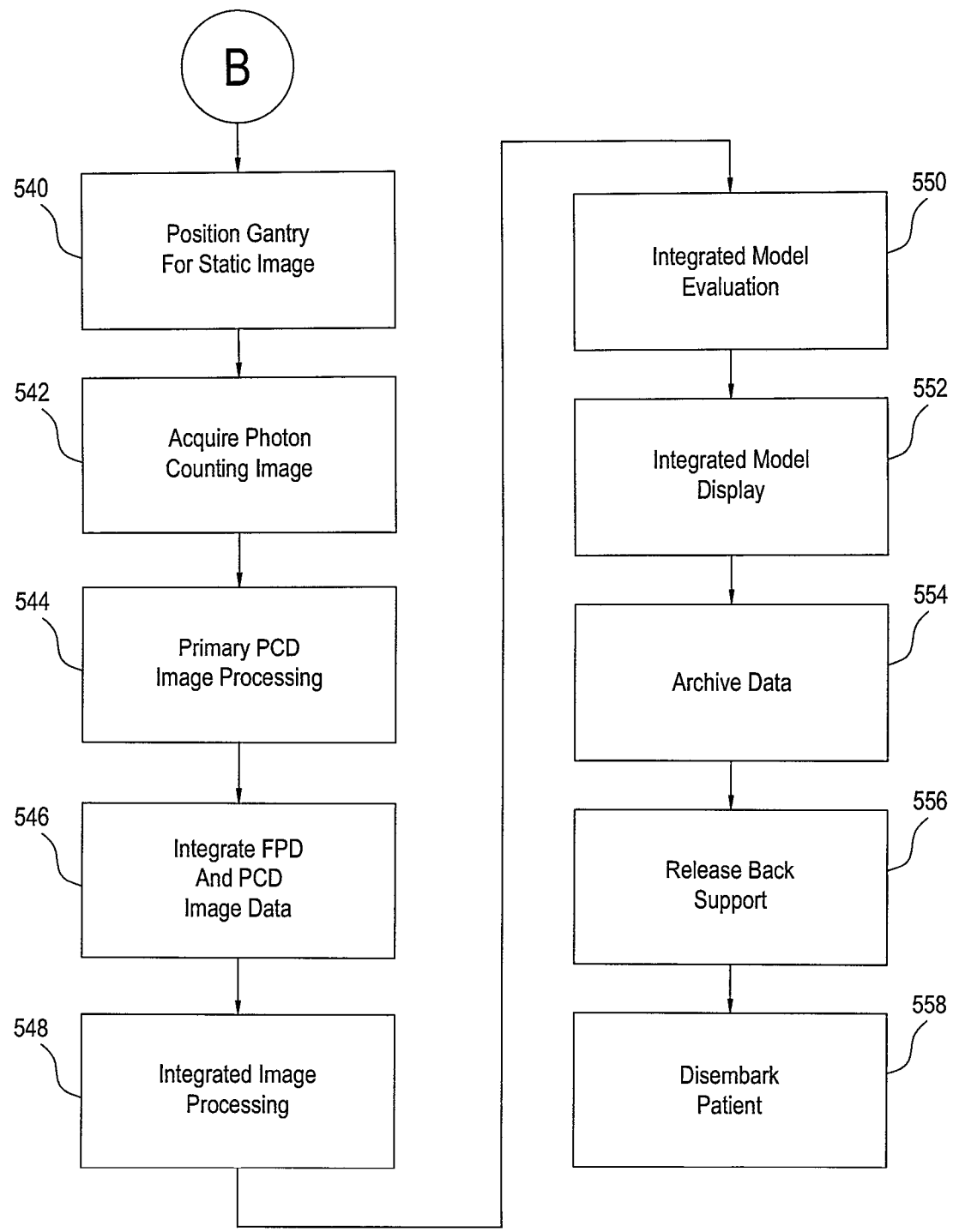
FIG. 5C shows in schematic block diagram form, still further aspects of a system and method for CBBCT imaging, including the imaging of breast calcification features.

FIGS. 5A-5C are intended to be considered concurrently and show, in functional flow diagram form, a method 500 of operating a CBBCT imaging system including calcification detection features as illustrated, for example, in FIGS. 2-4.

According to the illustrated exemplary embodiment of the invention, patient parameters (such as e.g., breast dimensions such as, length, circumference, transverse diameters, are secured 502, either by manual measurement of the patient, by extraction from patient medical records, or by automatic measurement. The parameter values, once secured, are optionally used to identify and select an appropriately sized breast stabilizer unit (or to prepare one, e.g., by subtractive or additive manufacturing methods). It will be appreciated that the use of a breast stabilizer unit is optional, and such a unit may not be employed in every embodiment of the invention or patient procedure. It will also be understood that, in certain embodiments of the invention, the dimensions of a breast stabilizer are adjustable, and are manually or automatically adjusted according to the patient parameters.

Where employed, the appropriately sized breast stabilizer is installed for operation 504, e.g., by coupling to a patient support panel through a coupler. Where consistent with a particular embodiment of the invention, signaling connections are made automatically or manually so as to couple instrumentation within the breast stabilizer to a system controller. Exemplary instrumentation will include accelerometers for identifying and characterizing breast vibration and motion, and electrodes for sensing muscle activity and/or cardiac activity. It will be appreciated, however, that a wide variety of other instrumentation will be employed according to the needs of a particular embodiment of the invention.

Preliminary adjustments are made to the patient interface panel and/or patient support features 506, and the patient ingress to the system 508 is effected. Thereafter, adjustment of the patient support features is finalized 510 so as to optimize patient comfort and stability. That is, with the patient disposed in situ, and the preliminary positioning completed, additional fixturing/support adjustments are made, i.e., additional patient parameters are ascertained from manual observation or automatic sensing of the patient body with respect to the system.

As discussed above, embodiments of the invention will include handgrips coupled to the patient support panel. Where available, in certain methods according to principles of the invention, the patient will be directed to grasp one or more of the handgrips 512. In certain embodiments of the invention, one or more handgrips will be instrumented to detect patient information such as, for example, the timing of the patient's heartbeat. As will be understood in light of the totality of the present disclosure, in certain embodiments of the invention, image acquisition is synchronized, with phase adjustment, to patient heartbeat so as to minimize motion-related blurring.

As noted in relation to FIG. 2, certain embodiments of the invention include a patient back support element (e.g., 292). Where present, and where deemed appropriate in relation to a particular patient and/or procedure, the patient back support element is activated 514 to stabilize patient positioning and minimize motion of the subject breast tissue during imaging.

In certain embodiments of the invention, patient sensing is initiated 516 once the patient is fully positioned. As discussed above in relation to, e.g., the handgrips 512 and breast stabilizer installation 504, patient sensing will, in certain embodiments, include sensing of patient breathing, heartbeat, muscular activity, or other patient parameters with the potential to influence image quality.

Thereafter, in certain embodiments of the invention, a static scout image (i.e., a preliminary image for establishing parameters and target position) is acquired 518. As will be appreciated by one of skill in the art, the static scout image will, in certain embodiments, provide information useful in establishing operating parameters of the system such as, e.g., preferred x-ray source positioning and power levels.

In certain embodiments of the invention, positioning actuators are operated 520 such as, e.g., the x-ray source radial positioning system 406, flat panel detector vertical actuator 428 and radial actuator 432, etc. After operation of the actuators, in a method according to certain embodiments of the invention, a shielding collimator, e.g., within the x-ray source, or as a separate apparatus (not shown) is operated to establish a desired cross-section of the x-ray beam.

In certain embodiments of the method of the invention, x-ray source parameters are set for imaging by, e.g., a flat-panel x-ray detector 522. In certain embodiments of the invention, the x-ray source will offer the option of a 0.1 mm focal spot or a 0.3 mm focal spot. In certain embodiments of the method of the invention the setting of x-ray source parameters includes configuring the x-ray source to produce a 0.3 mm focal spot for tomographic imaging with the flat-panel detector.

Thereafter, in certain embodiments of the method of the invention, rotation of the rotary gantry is initiated 524 and tomographic image data is acquired 526 with the flat-panel detector.

Tomographic image data is transferred from the flat-panel detector to the processor and the image data from the flat-panel detector is processed 528 to produce a tomographic image data set.

In certain embodiments, the processed data is immediately used to identify characteristics of the breast including, for example, calcifications and lesions. In some circumstances these represent newly identified breast features. In other circumstances the CBBCT image data is used to precisely locate features previously discovered and, in some instances, to guide supplemental procedures such as, for example aspirated needle biopsy, or other procedures.

In certain embodiments of the invention, the tomographic image data set is further evaluated to identify regions of interest 530 for supplemental imaging. In respective embodiments of the invention, this further evaluation will include image enhancement processing, human review and evaluation of images, and/or automatic review and evaluation of images by conventional image processing software and/or deep learning artificial intelligence processing software.

In certain embodiments of the invention, the tomographic image data set is configured for display, and displayed to a user such as a technician, a clinician, or other evaluating personnel. In certain embodiments of the invention, the displayed information is annotated to include features identifying regions of interest and displayed with the annotation 532. Such regions of interest will be, in certain embodiments of the invention, regions where characteristics of possible or likely calcification are present.

In certain embodiments of the invention, the user is presented with an opportunity to provide input 534 to the system including, without limitation, input identifying regions of greater or lesser interest, including regions within the annotated regions of interest, and other regions not annotated by the system. In certain embodiments of the system, the regions annotated for additional evaluation will be automatically subjected to additional imaging. In certain embodiments of the invention, regions identified by the user will be subjected to additional imaging. Additional imaging will be, in respective embodiments of the invention, one or more of additional tomographic imaging with a flat-panel detector, additional tomographic imaging with a photon counting detector, additional stationary imaging with a flat-panel detector, and additional stationary imaging with a photon counting detector.

Accordingly, in certain embodiments of the invention, the imaging system will activate a photon counting detector position actuator 536 to position the photon counting detector for imaging of a region of interest. In certain embodiments, the system (e.g., a control processor), will set parameters of the x-ray source 538 for imaging with a photon counting detector. In certain embodiments of the invention, the parameters of the x-ray source will include parameters positioning collimator plates to selectively illuminate a region of interest with x-rays produced by the x-ray source. In certain embodiments of the invention, the parameters of the x-ray source will include parameters setting focal spot size. In certain embodiments of the invention the focal spot size selected for illuminating the photon counting detector will be a focal spot size having a diametric dimension of 0.1 mm.

According to certain embodiments of the invention, the gantry will rotate 540 a rotational distance effective to align an x-ray beam axis of the x-ray source with a selected region of interest. The x-ray source will be operated to produce a pulse of x-rays. The pulse of x-rays will pass through a region of interest of the subject breast, and the photon counting detector will receive photons of the x-ray pulse to acquire a photon counting image 542.

Data corresponding to the acquired photon counting image will be received from the photon counting detector at a processor, and the processor will conduct primary image processing 544 of the photon counting detector data.

The processor will then integrate the flat-panel detector data and photon counting detector data 546 and conduct integrated image processing of the combined data sets 548 such as, for example and without limitation, Fourier transform processing, Laplace transform processing, edge identification processing, etc.

The resulting processed image data, comprising an integrated model, will be evaluated 550 by human personnel and/or by automated image evaluation systems including, without limitation, artificial intelligence/deep learning image evaluation systems, to identify diagnostic and/or other features of the breast, including, for example, calcification features.

The resulting integrated model, optionally including identified diagnostic and/or other features of the breast will be displayed 552 as two-dimensional and/or three-dimensional image data including, where appropriate, artificial color, wireframe modeling, grayscale imaging, and other imaging as is known, or becomes known, in the art.

In certain embodiments of the invention, the integrated model, as well as preliminary data and/or intermediate data will be archived 554, in a digital patient record or otherwise, for future reference.

According to the method of the invention, where employed, the patient back support features will be returned to initial condition 556, and the patient disembarked 558 from the imaging system.

It will be appreciated by one of skill in the art that various elements of the method presented above are optional. Alternative aspects of the overall imaging systems methods and apparatus described herewith are to be applied in various embodiments of the method that will be evident in light of the totality of the present disclosure.

It should be further noted that in some cases, in situ breast marking, or anticipatory registration marking is effected so as to facilitate integration of data sets and/or, to aid in the application of supplemental procedures such as diagnostic, biopsy and/or treatment activities. In certain embodiments, registration marks will be provided integral to the breast stabilization unit. In other embodiments of the invention, registration marks will be provided by ink marking on the breast being imaged, by the application of an adhesive sticker including an x-ray opaque or x-ray translucent element, by the application, by adhesive or otherwise, of a vitamin E capsule at or to the skin of the breast, or by any other method known, or that becomes known, in the art.

Figure 6:
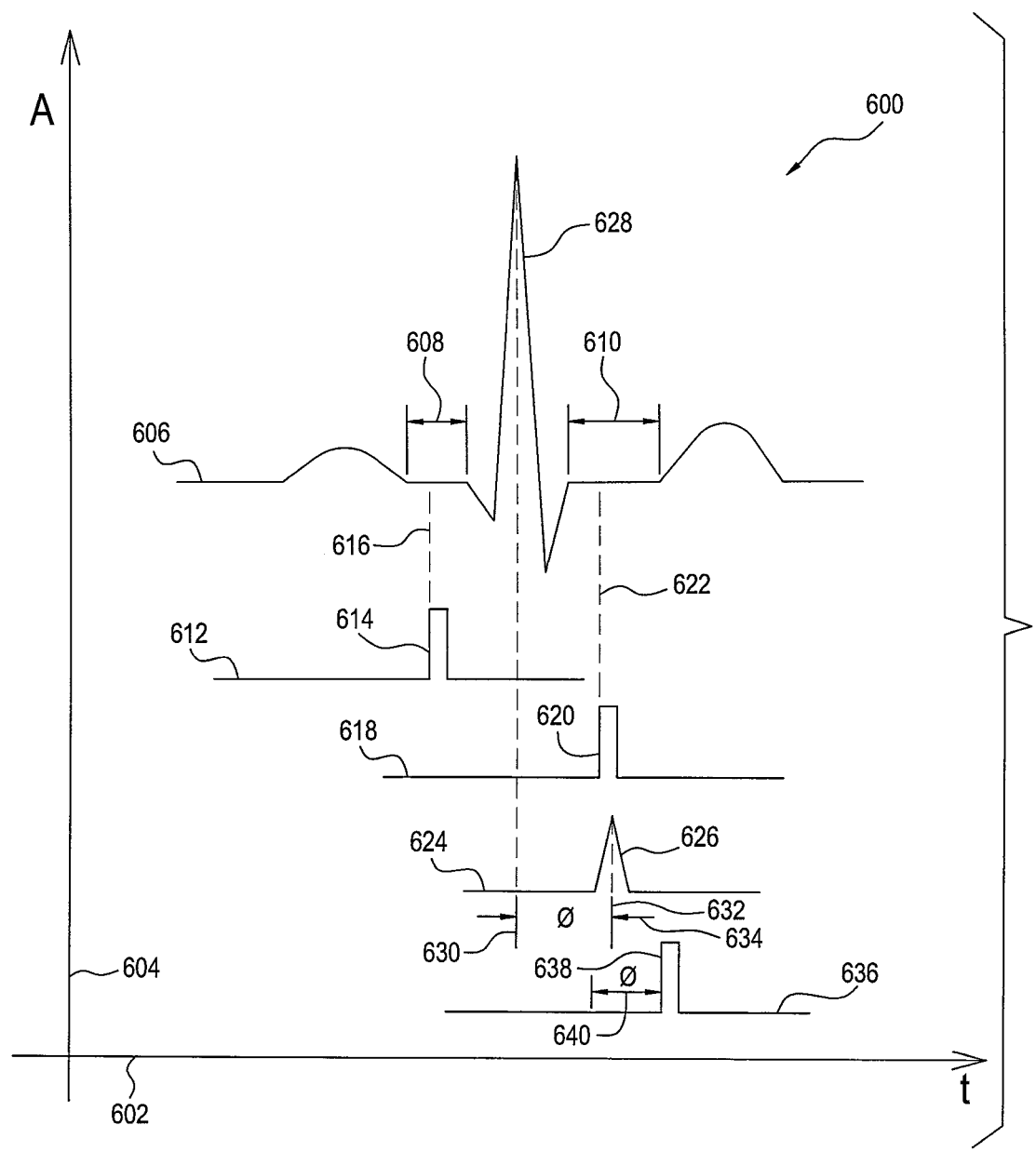
FIG. 6 shows, as a schematic graphical plot, timing aspects of a system and method for CBBCT imaging, including the imaging of breast calcification features.

FIG. 6 shows, as a schematic graphical plot 600, timing relationships between a patient heartbeat and imaging pulses for an imaging system prepared according to principles of the invention. Accordingly, horizontal axis 602 indicates time, and a vertical axis 604 corresponds to the respective amplitude of the graphically indicated signals.

A schematic representation of a normal sinus heartbeat waveform is shown 606. As will be appreciated by one of skill in the art, waveform 606 includes a PR segment during a first interval 608 and a ST segment during a second time interval 610. As is evident upon inspection, the waveform during time intervals 608 and 610 is relatively quiescent, as compared with the balance of the waveform.

Plot 612 shows an exemplary triggering signal for an x-ray source employed in a CBBCT imaging system prepared according to principles of the invention. One of skill in the art will appreciate that the indicated pulse 614 corresponds to x-ray emission and/or image acquisition of an individual x-ray image by the system. The reader will appreciate that, upon biometric acquisition of the patient heartbeat signal, the imaging pulse 614 can be synchronized 616 to the relatively quiescent PR segment during time interval 608. Accordingly, blurring caused by the movement of patient breast tissue in response to the patient heartbeat can be reduced. Beneficially, this reduction in blurring will allow improved calcification detection.

In a different embodiment according to principles of the invention (or in the same embodiment with different operating parameters), signal 618 illustrates a similar triggering pulse 620 synchronized 622 the relatively quiescent ST segment of time interval 610. One of skill in the art will appreciate that image acquisition will, in various embodiments of the invention, be synchronized to time interval 608 or 610, according to various design and/or procedural considerations. In certain embodiments of the invention, where relatively high speed imaging is required, it will be possible to acquire x-ray images during both PR 608 and ST 610 segments of a single heartbeat waveform.

Plot 624 provides a schematic representation of, for example, an accelerometer signal. In one exemplary embodiment of the invention, the accelerometer signal is produced by an accelerometer disposed in contact with a surface region of the breast being imaged. In certain embodiments of the invention, the accelerometer is coupled to, or integrally formed with, a breast stabilization unit. In other embodiments of the invention, the accelerometer is placed in contact with the patient breast prior to patient ingress to the system by, for example, an adhesive device. One of skill in the art will understand that alternative sensing technologies, such as ultrasonics or lidar may be employed to sense the heartbeat signal at the breast.

The accelerometer signal 624 includes a pulse signal 626 motivated by, and corresponding to, the QRS complex pulse 628 of the heartbeat waveform 606. By detecting, for example through EKG monitoring, the timing 630 of the QRS complex pulse 628, and the corresponding timing 632 of the accelerometer pulse signal 626, a phase shift (delta t) 634 can be ascertained. One of skill in the art will appreciate that the time interval delta t corresponds to the travel time interval between the generation of the acoustic signal at the heart and its arrival at the tissue of the breast. By applying 640 this phase shift 634 to the pulse 620 of signal 618 an improved signal 636 can be generated wherein imaging pulse 638 corresponds to pulse 620 shifted (delayed) by the time interval of phase shift 634.

Alternately, in certain embodiments of the invention the accelerometer signal 624, 626 is used to identify a quiescent condition of the tissue at the breast, and is used directly to control image acquisition.

One of skill in the art will, of course, appreciate that whereas signal 606 is generally periodic, signal 612, 618 and 636 will be active where desirable in relation to both the quiescent state of the breast tissue, and the angular position of the imaging apparatus. The practitioner of skill in the art will also understand that while the foregoing description addresses cardiac rhythms and related image acquisition timing compensation, other embodiments of the invention will similarly address pulmonary rhythms and image acquisition timing as well as other periodic and aperiodic motions of the imaging subject. Such compensation schemes will be readily apparent to the skilled practitioner in light of the present disclosure, and are intended to be enabled by this presentation.

Figure 7:
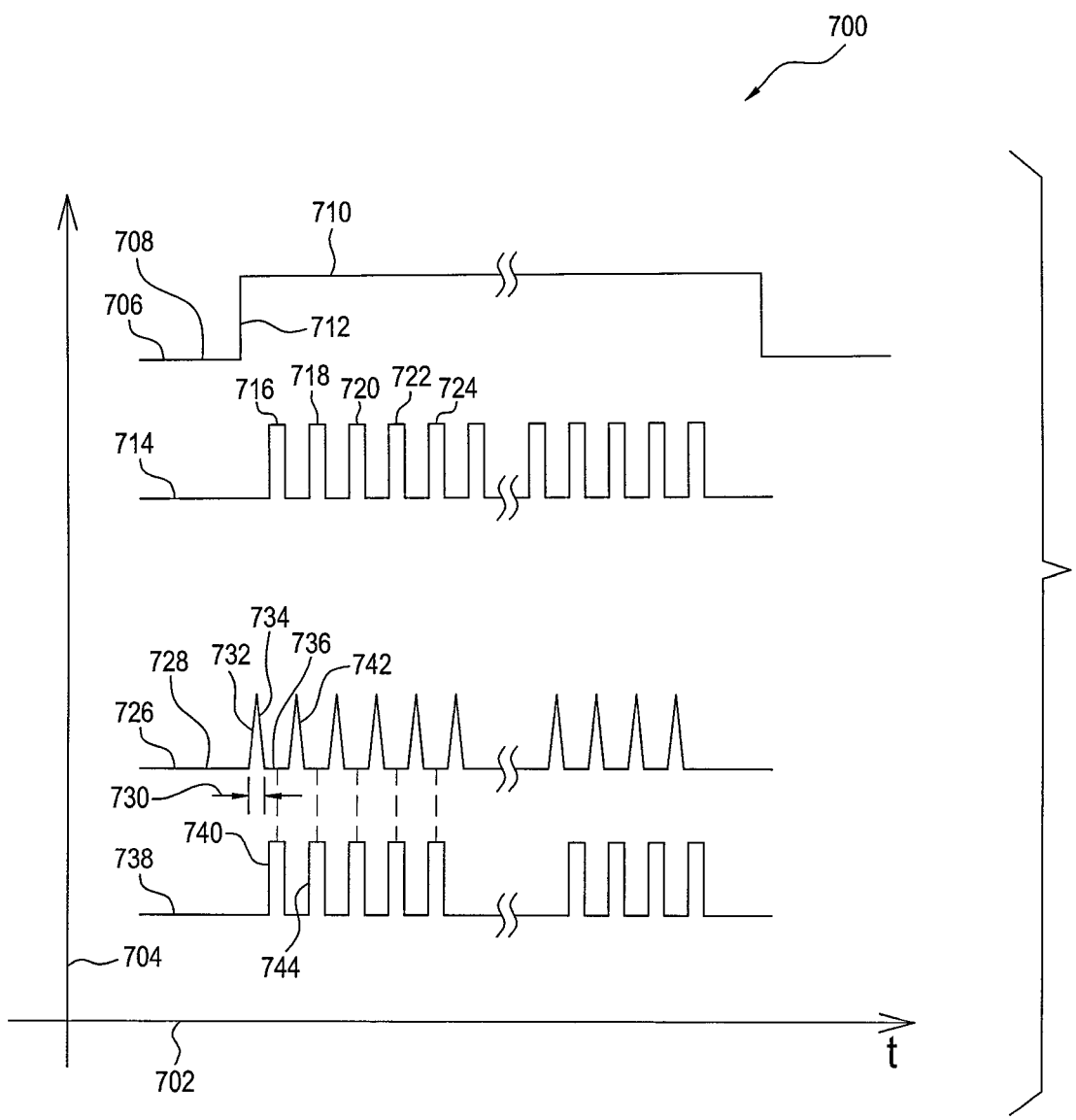
FIG. 7 shows, as a schematic graphical plot, additional timing aspects of a system and method for CBBCT imaging, including the imaging of breast calcification features.

Referring now to FIG. 7, as noted above, in existing CBBCT systems, an imaging gantry is rotated continuously through, for example, 180° plus cone width, or 360° plus cone width during imaging. During rotation of the gantry, images are periodically acquired at an x-ray detector (e.g., at 2° intervals). One of skill in the art will understand that, because the image acquisition time is small but finite, and because the x-ray detector is continuously in motion during image acquisition, a certain amount of blurring is introduced into the acquired image.

Accordingly, certain embodiments of an improved CBBCT system prepared according to principles of the invention include an image acquisition apparatus that is arrested and substantially static with respect to the breast being imaged during each image acquisition cycle.

FIG. 7 shows, as a schematic graphical plot 700, timing relationships between a rotary motion of an imaging system for a CBBCT system according to principles of the invention and imaging pulses for the imaging system. Accordingly, horizontal axis 702 indicates time, and a vertical axis 704 corresponds to a state of the respective system element.

The motion of a continuously-moving imaging gantry as shown by plot 706, where the gantry is either in a first state 708 that is static with respect to the breast being imaged, or a second state 710 that is in motion with respect to the breast being imaged. After completing this rotation, the apparatus returns to a static state 708. Although the transition between states 712 is shown idealized as substantially instantaneous, one of skill in the art will appreciate that time is actually required to accelerate and decelerate the imaging apparatus.

Plot 714 represents imaging cycles of the imaging apparatus of plot 706. That is, each pulse, e.g., 716, 718, 720, 722, 724 etc. represents a pulse of x-ray energy and a corresponding image acquisition by the system. As will be appreciated by the reader, the plurality of images corresponding to pulses 716-724, etc., are processed to produce a tomographic image.

In contrast, plot 726 represents the motion of an imaging gantry prepared according to principles of the invention. As shown, the gantry begins in a state 728 that is static with respect to the breast being imaged. During a first time interval 730, the gantry accelerates 732 and then decelerates 734, resulting in an angular rotation step of the gantry. The gantry is then maintained substantially static 736 with respect to the breast being imaged. While the imaging system is static 736, an imaging signal 738 is pulsed 740 to produce an x-ray pulse and acquire an image. Thereafter, the gantry is again rotated 742 through a finite step, after which a further imaging cycle 744 is signaled.

Upon consideration of the plots of FIG. 7, one of skill in the art will immediately appreciate that the interleaved cycles of gantry motion and image acquisition ensure that the gantry is substantially still every time an image is acquired. As a result, the blurring associated with gantry motion during image acquisition is reduced or eliminated and overall tomographic image quality is improved. This improvement in image quality, in conjunction with the other improvements presented herewith, serves to increase the effective resolution and clarity of system images, and improve the ability of the system to detect diagnostically significant breast calcifications.

In order to achieve the motion profile represented by plot 726, the respective masses of the gantry and imaging equipment (including x-ray source and x-ray detector) are minimized. Feedback and feedforward control, along with principles of modern control theory, are applied to size motors and other system components, generate desired control signals, and minimize undesirable resonances within the system. In certain embodiments of the invention, the frequency of pulses in plot 738 may be selected to be lower than the corresponding frequency in plot 714. In other embodiments, a half circle scan (1800 plus cone width) will be employed instead of a full circle scan. In some embodiments, this approach will nevertheless imply a longer overall CBBCT image acquisition time. In certain embodiments of the invention, however, this longer image acquisition time will be justified by improved imaging and resulting ability to effectively image microcalcifications within the subject breast.

Figure 8A:
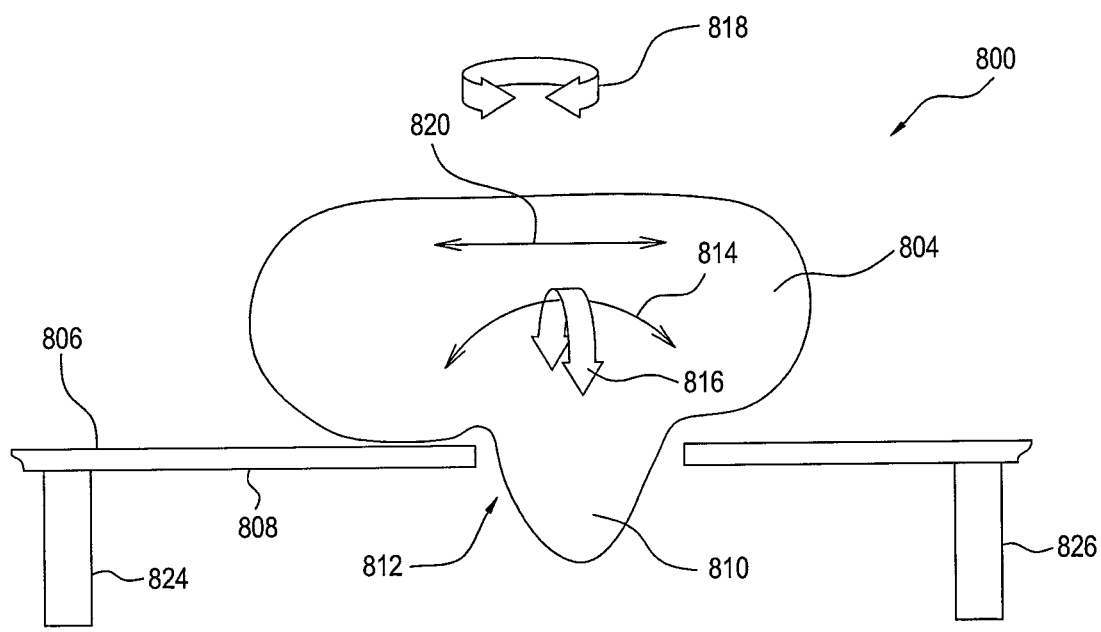
FIG. 8A shows, in schematic cross-sectional elevation, a portion of a CBBCT breast imaging system, including aspects of an exemplary patient stabilization system.
Figure 8B:
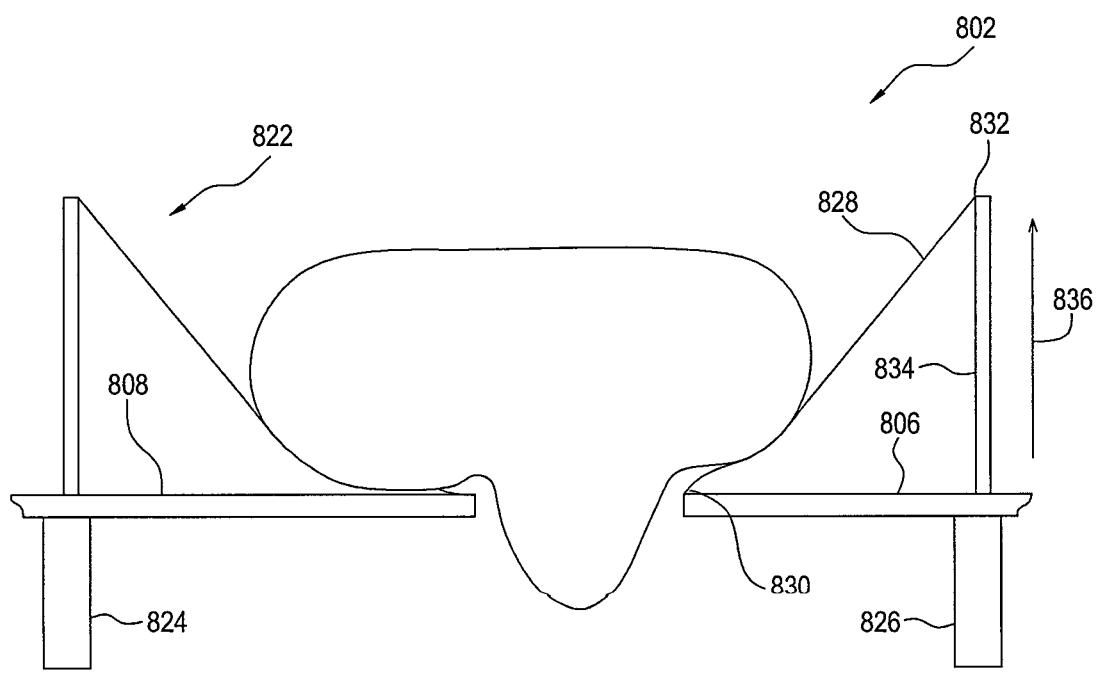
FIG. 8B shows, in schematic cross-sectional elevation, a portion of a CBBCT breast imaging system, including further aspects of an exemplary patient stabilization system.

FIGS. 8A and 8B show, in schematic cross-sectional elevation, respective inactive 800 and active 802 configurations of a dynamic patient support system for a CBBCT imaging system prepared according to principles of the invention. In FIG. 8A a patient chest 804 is shown in cross-section. The patient is shown disposed on an upper surface 806 of a patient interface panel 808. The patient's breast to be imaged 810 is disposed through an aperture 812 of the patient interface panel 808.

The patient is relatively unconstrained on the patient interface panel. Accordingly, the chest of the patient will tend to roll 814, pitch, 816, yaw 818 and translate 820 in various directions in response to voluntary and involuntary actions of the patient. These motions will result in corresponding rotations, translations and vibrations of the subject breast 810, displacing the tissue of the breast dynamically during imaging.

As discussed above, such displacement of the breast during imaging tends to blur the resulting image, i.e., introduce error into the corresponding image data. Consequently, effective imaging of microcalcifications within the breast tissue is facilitated by increased stabilization of the patient chest, and the patient body overall.

In certain embodiments of the invention, this stabilization will be achieved by the manual insertion of, for example, one or more wedge, or other shaped, bolsters around the patient after patient ingress to the system and prior to imaging. Discrete and/or independent bolsters, however, may be readily displaced by the patient. In addition, the overall time for the procedure may be extended by the bolster insertion process. The patient may become impatient, reducing patient satisfaction and, for example, screening compliance. In addition, overall time for the imaging procedure will be extended, resulting in additional costs.

Accordingly, in certain embodiments of the invention, an automated patient bolstering apparatus 822 is provided as a dynamic patient support system. In the exemplary embodiment illustrated, the automated patient bolstering apparatus 822 includes one or more linear actuators, e.g., 824, 826 mechanically coupled to the patient interface panel 808.

In the exemplary embodiment, a flexible member 828 is coupled at a first region 830 to the patient interface panel 808 and at a second region 832 to a mobile portion, e.g., 834 of the linear actuator, e.g., 826.

When the linear actuator transitions from an inactive configuration (as shown in FIG. 8A) to an active configuration (as shown in FIG. 8B), the mobile portion 834 of the linear actuator 826 extends in a direction 836 away from the patient interface panel 808. Consequently, the flexible member 828 is placed in tension. The flexible member 828, thus placed in tension, tends to gently support and confine the patient chest 804, thereby stabilizing the patient, and reducing undesirable motion of the breast tissue.

In certain embodiments of the invention, the transition of the patient support system from an inactive configuration to an active configuration and back again will be controlled by, for example, an operator, a technician, and/or a clinician. In other embodiments of the invention, the transition from an inactive configuration to an active configuration and back again will be controlled by the patient. In other embodiments of the invention, the transition from an inactive configuration to an active configuration and back again will be controlled by a controller, generally in the nature of controller 254 described above.

One of skill in the art will appreciate that, while the illustrated embodiment includes a mechanical linear actuator, other bolstering methods and apparatus such as, for example and without limitation, one or more pneumatic bladders and/or one or more hydraulic bladders, and any other appropriately functioning actuator component that is known or becomes known in the art, may be used.

In certain embodiments of the invention, the linear actuator will include, merely for example and without limitation, one or more of an electrical solenoid, a pneumatic cylinder, a hydraulic cylinder, a pneumatic bladder, a hydraulic bladder, a linear electric motor, a linear stepping motor, a rotary actuator along with: an Acme screw and nut, a lead screw, a ballscrew, a cable, a pulley, a timing belt, a timing pulley, an appropriately sized worm gear reducer, a rack and pinion assembly, a rack and worm gear assembly, a piezoelectric actuator, a piezoelectric actuator combined with a ratchet and pawl driver, a spring loaded actuator, and actuator including a shape metal alloy, and any other appropriately functioning actuator component that is known or becomes known in the art.

In certain embodiments of the invention, the linear actuator will be manually activated. In other embodiments of the invention, the linear actuator will be driven by a motor such as, for example, an electric motor, a pneumatic motor, a hydraulic motor, a spring, or any other motivating device such as is known or becomes known in the art.

In respective embodiments of the invention, the flexible member 828 will include, for example and without limitation, any of a synthetic polymer, a natural polymer, a textile, a molded material, a woven material, an extruded material, a braided material, and a felted material, and combinations thereof. In addition, the flexible member 828 will include, for example and without limitation, any of polyamide, polypropylene, polyethylene, including low-density polyethylene, medium density polyethylene, high density polyethylene and ultrahigh molecular weight polyethylene, polyaramid, polyester, polytetrafluoroethylene, leather, cotton, wool, linen, flax, and/or any related material, and combinations thereof.

Elastomers that may be used in various embodiments of the invention include various copolymers or block copolymers (Kratons®) available from Kraton Polymers such as styrene-butadiene rubber or styrene-isoprene rubber, EPDM (ethylene propylene diene monomer) rubber, nitrile (acrylonitrile butadiene) rubber, polyurethane, polybutadiene, polyisobutylene, neoprene, natural latex rubber and the like. Foam materials may be closed cell foams or open cell foams, and may include, but is not limited to, a polyolefin foam such as a polyethylene foam, a polypropylene foam, and a polybutylene foam; a polystyrene foam; a polyurethane foam; any elastomeric foam made from any elastomeric or rubber material mentioned above; or any biodegradable or biocompostable polyesters such as a polylactic acid resin (comprising L-lactic acid and D-lactic acid) and polyglycolic acid (PGA); polyhydroxyvalerate/hydroxybutyrate resin (PHBV) (copolymer of 3-hydroxy butyric acid and 3-hydroxy pentanoic acid (3-hydroxy valeric acid) and polyhydroxyalkanoate (PHA) copolymers; and polyester/urethane resin. One of skill in the art will appreciate that the foregoing are merely exemplary of a wide variety of possibilities that would be applied in an appropriate applications.

Figure 9A:
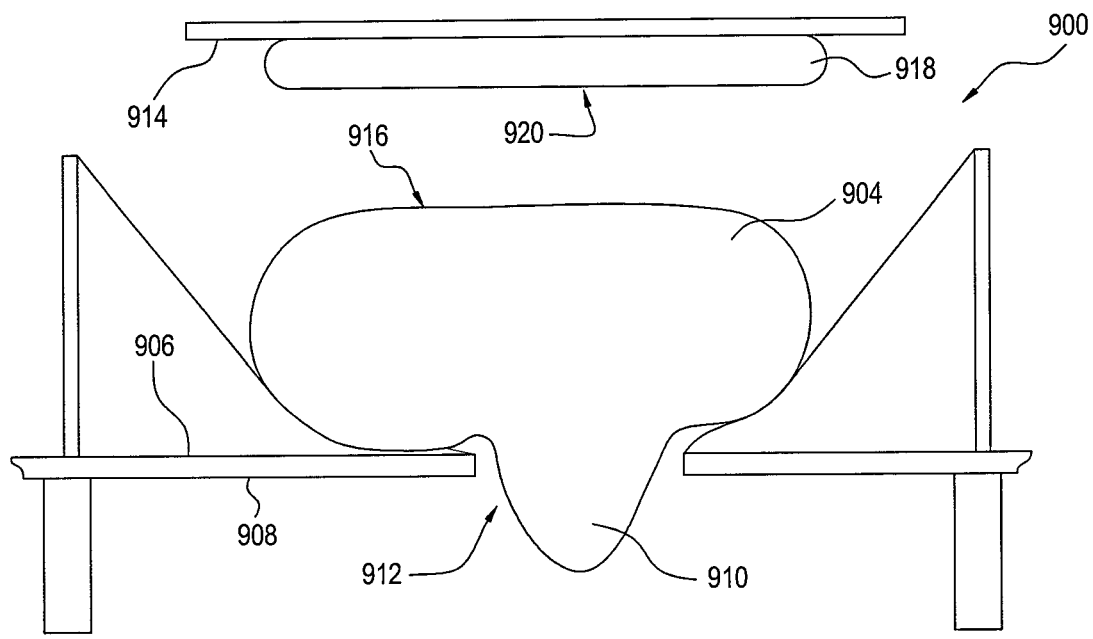
FIG. 9A shows, in schematic cross-sectional elevation, a portion of a CBBCT breast imaging system, including aspects of an exemplary back support element.
Figure 9B:
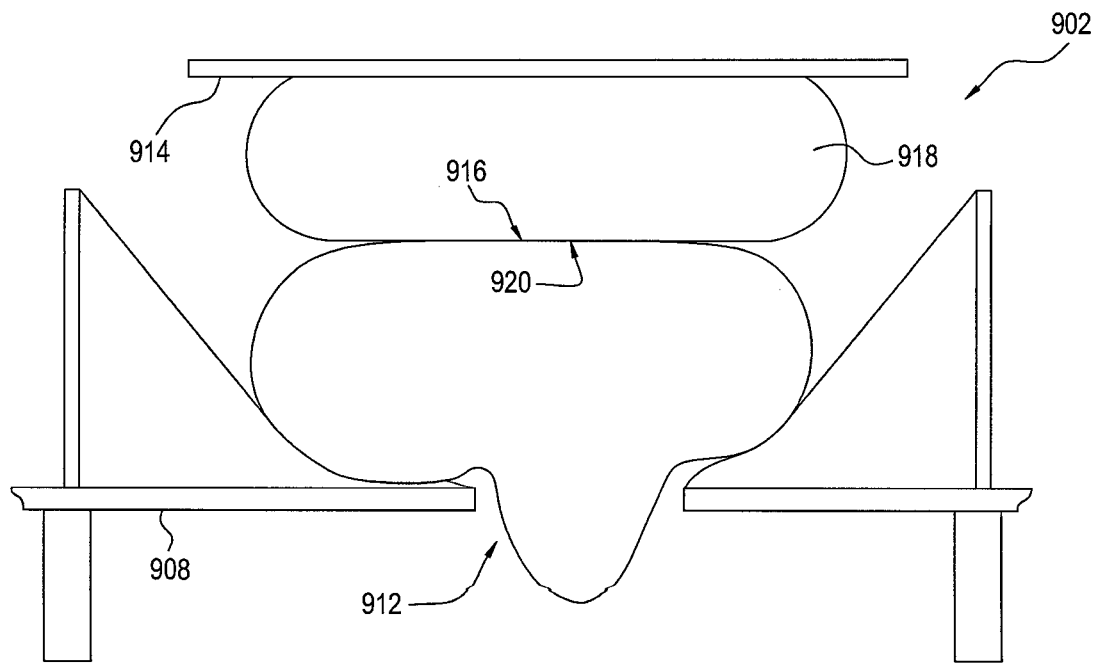
FIG. 9B shows, in schematic cross-sectional elevation, a portion of a CBBCT breast imaging system, including further aspects of an exemplary back support element.

FIGS. 9A and 9B show, in schematic cross-sectional elevation, respective inactive 900 and active 902 configurations of a patient back support element for a CBBCT imaging system prepared according to principles of the invention. In FIG. 9A a patient chest 904 is shown in cross-section. The patient is shown disposed on an upper surface 906 of a patient interface panel 908. The patient's breast to be imaged 910 is disposed through an aperture 912 of the patient interface panel 908.

A structural member 914 is disposed in spaced relation to a back surface region 916 of the patient. When in operation, the structural member is supported in substantially fixed spatial relation to the patient interface panel 908. It should be noted, however, that the structural member 914 may be, in certain exemplary embodiments of the invention, removable, and/or displaceable by, for example and without limitation, pivoting, sliding, elevating, rolling, etc., so as to facilitate patient ingress and egress with respect to the CBBCT imaging system.

As illustrated, structural member 914 supports a bolstering element. In the illustrated embodiment, the bolstering element is an inflatable bladder 918 such as, for example, a pneumatically inflatable bladder and/or a hydraulically inflatable bladder. In the illustrated embodiment, the inflatable bladder 918 is shown in FIG. 9A in a first inactive configuration, and in FIG. 9B in an active configuration. In the inactive configuration, the inflatable bladder is deflated, and in the active configuration, the inflatable bladder is inflated.

In the inflated configuration, a surface region 920 of the inflatable bladder 918 is disposed in contact with a corresponding portion of the back surface region 916 of the patient. In this configuration, the inflatable bladder 918 tends to urge the back surface region 916 of the patient towards the aperture 912 of the patient support panel 908. This arrangement tends to constrain patient motion and diminish blurring image artifacts in the manner generally described above.

While the illustrated embodiment shows a discrete structural member 914 and an inflatable bladder 918, a wide variety of configurations and arrangements will become immediately apparent to one of skill in the art in light of the suggestion provided by the present disclosure. Thus, for example, in certain embodiments of the invention, the inflatable bladder 918 will be replaced by, for example, an upholstered pad, and the structural member 914 will transition towards and away from the back surface region 916 of the patient in response to, for example and without limitation, a linear actuator mechanically coupled between the structural member 914 and the patient support panel 908. In other embodiments of the invention, cushioning may be omitted altogether.

In certain embodiments of the invention, the transition of the patient back support element from an inactive configuration to an active configuration and back again will be controlled by, for example, an operator, a technician, and/or a clinician. In other embodiments of the invention, the transition from an inactive configuration to an active configuration and back again will be controlled by the patient. In other embodiments of the invention, the transition from an inactive configuration to an active configuration and back again will be controlled by a controller, generally in the nature of controller 254 described above.

Figure 10:
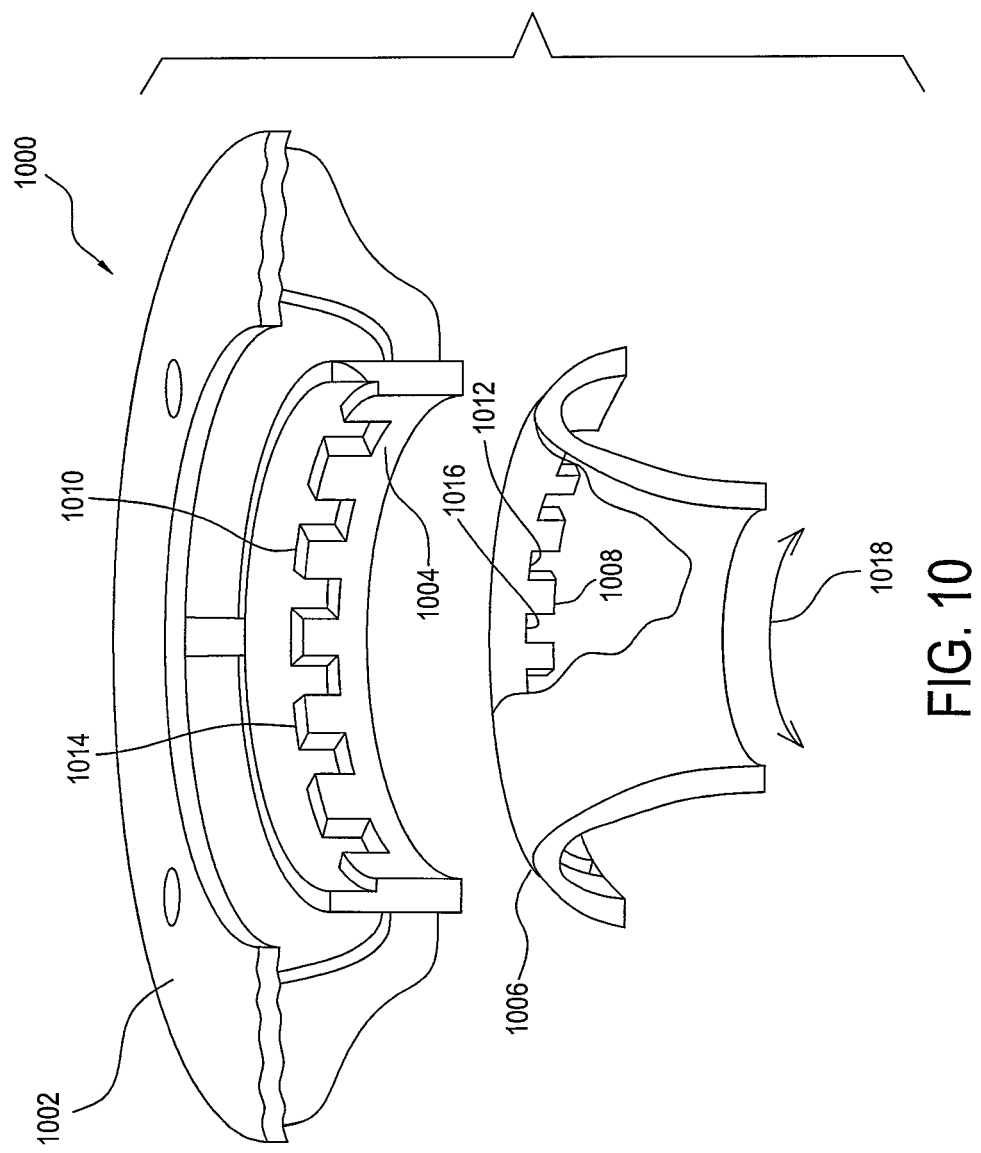
FIG. 10 shows in schematic cutaway perspective view, certain aspects of an exemplary CBBCT breast imaging system including portions of a coupling feature of a receiver and breast stabilizer unit prepared according to principles of the invention.

In light of the foregoing disclosure, FIG. 10 shows, in cutaway schematic perspective view, a portion 1000 of a breast imaging system including certain aspects of an interface between a receiver apparatus and a breast stabilizer unit. Specifically, FIG. 10 shows a portion of receiver apparatus 1002 including a receiver coupling feature 1004, and a breast stabilizer unit 1006 including a corresponding breast stabilizer unit coupling feature 1008.

In the exemplary apparatus of FIG. 10, the receiver coupling feature 1004 and breast stabilizer coupling feature 1008 include complementary crenellated surface regions 1010, 1012 respectively. One of skill in the art will readily appreciate that the generally rectangular projections, e.g., 1014 of the receiver coupling feature 1004 will be sized and configured to be received snugly within the corresponding generally rectangular recesses 1016 of the breast stabilizer unit coupling feature 1008, and vice versa.

Moreover, it will be apparent to one of skill in the art that where, in certain embodiments, the sizing of the various crenellations are generally uniform, a wide variety of symmetric placements of the breast stabilizer unit with respect to the receiver will be possible. Thus, a rotational adjustment of the breast stabilizer unit about a longitudinal axis of the receiver unit (and thus, in certain embodiments, about an axis of rotation 1008 of the gantry 1004) will be facilitated.

This will be of particular value in an embodiment where an asymmetric characteristic of the breast stabilization unit is chosen to conform to a corresponding asymmetry of the patient's breast. Thus, the breast support unit can be rotated 1018 until it is properly aligned with the patient's breast as the patient lies prone on the patient support panel.

Figure 11:
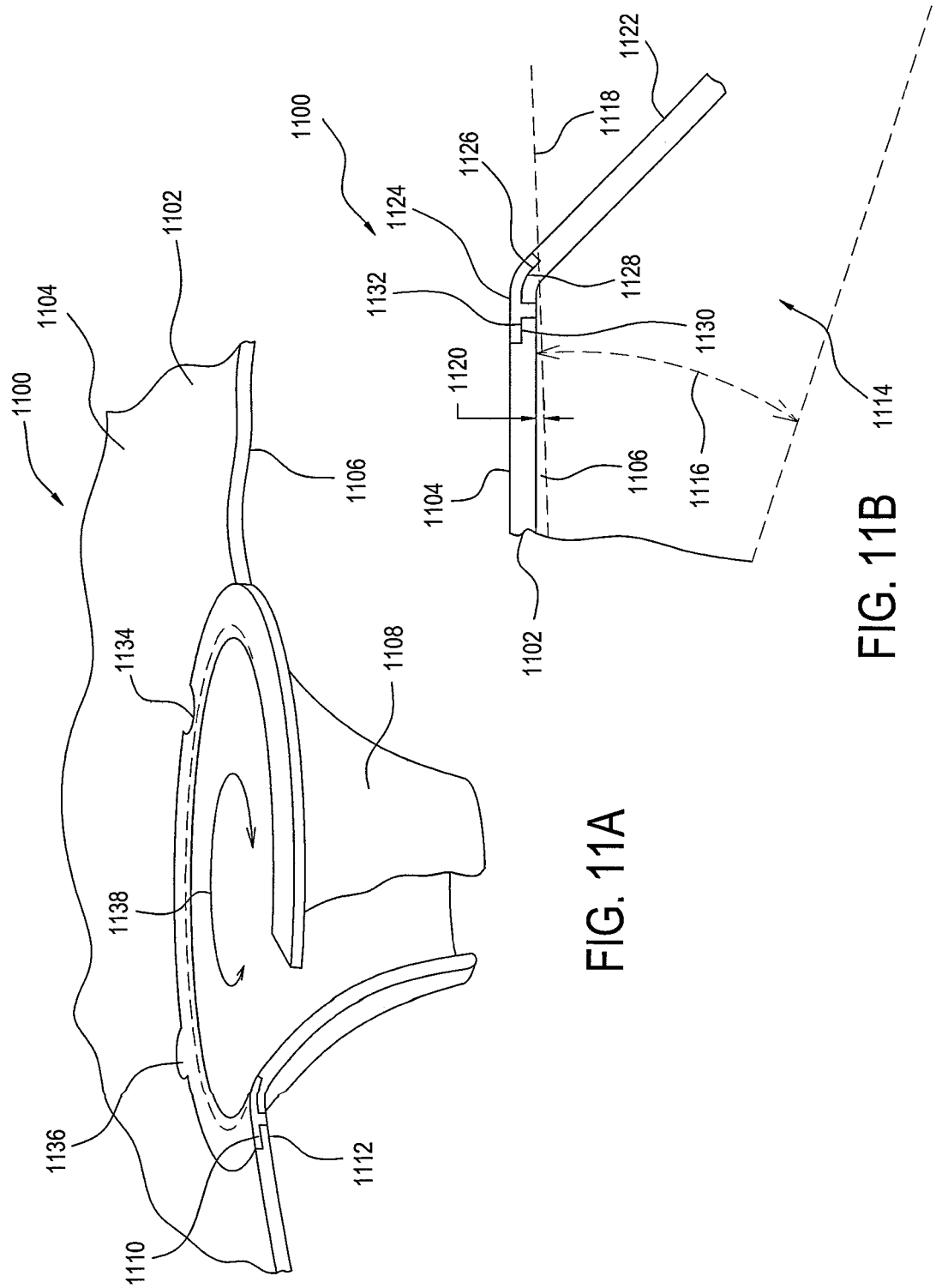
FIG. 11A shows in schematic cutaway perspective view, certain aspects of an exemplary CBBCT breast imaging system including certain aspects of an exemplary breast stabilizer unit prepared according to principles of the invention.
FIG. 11B shows in schematic cross-sectional detail elevation, additional aspects of an exemplary CBBCT breast imaging system including certain aspects of an exemplary breast stabilizer unit prepared according to principles of the invention.

FIG. 11A shows, in schematic perspective cutaway view, further aspects and characteristics of an exemplary imaging system 1100 prepared according to principles of the invention. As illustrated, the imaging system includes a patient support panel 1102 with an upper surface 1104 and a lower surface 1106. Imaging system 1100 presents certain particularly desirable features including a breast stabilization unit 1108 that is prepared and configured to allow imaging of substantially the entire subject breast and, in some cases, a portion of the corresponding chest wall while effectively stabilizing the breast for calcification detection.

Rather than having a discrete receiver, the illustrated embodiment shows a surface region 1110 of the patient support panel 1102 that serves as a receiver coupling region 1112.

Referring now to FIG. 11B in conjunction with FIG. 11A; FIG. 11B shows in schematic cross-sectional view, further detail of the exemplary imaging system 1100. As noted above, patient support panel 1102 includes an upper surface region 1104 and a lower surface region 1106.

When in operation, an x-ray beam 1114 fills a spatial region below surface 1106 and spans 1116 a cross-sectional area designed and configured to illuminate a target region of the subject breast, up to and including the entire breast.

It should be understood that, in certain applications of the imaging system 1100, it is desirable for an upper boundary 1118 of the x-ray beam 1114 to be disposed as close as possible to lower surface 1106 of patient support panel 1102 (i.e., minimizing or optimizing distance 1120), so as to permit imaging of the breast as near as possible or practical to the patient's chest wall. Indeed, in certain embodiments of the invention, it will be possible to image a portion of the chest wall with the imaging system 1100.

In the illustrated embodiment, the breast stabilization unit 1108 includes a first body element 1122 and a second rim element 1124. The first body element 1122 will include, in certain embodiments, a structural material having mechanical characteristics sufficient to support a patient breast and a material that is relatively x-ray transparent. In certain embodiments of the invention, a single material will embody both of these characteristics.

In certain embodiments of the invention, the first body element 1122 will be substantially fixedly coupled to the second rim element 1124 at respective interface surface regions 1126, 1128. In respective embodiments this coupling will be achieved through the use of a chemical adhesive, a physical bond, a mechanical fastener, mechanical swaging, a weld, such as a thermal weld, an ultrasonic weld, a laser weld, or a chemical weld, or any other coupling mechanism appropriate to the requirements of the application, including any combination thereof.

In the illustrated example the second rim element 1124 includes a rim coupling surface region 1130. The rim coupling surface region 1130, is adapted and configured to interface with a complementary patient support panel coupling surface region 1132, to form a secure coupling between the patient support panel 1102 and the breast stabilization unit 1108.

As per the illustrated example, the characteristics of the materials selected, and the configuration of those materials allow the patient support panel 1102 to support the breast stabilization unit 1108 without substantially interfering with the upper boundary 1118 of the x-ray beam 1114. The materials of the second rim element 1124 will thus be selected accordingly and will, in respective embodiments, include any of a metallic material, a synthetic polymer material, a glass material, a natural polymer material, or any other structural material appropriate to the requirements of a particular embodiment, including combinations thereof.

In the illustrated example, the second rim element 1124 is keyed 1134, 1136 to the patient support panel 1102 to limit rotation 1138 of the breast stabilization unit 1108 about a longitudinal axis thereof. However, in other embodiments of the invention, the design, materials and configuration of the second rim element 1124 and the corresponding coupling surface region 1132 of the patient support panel 1102 will be selected and configured to allow frictional rotation, or substantially free rotation of the breast stabilization unit 1108.

It will also be appreciated that the second rim element 1124 will, in respective embodiments, have respective radial dimensions such that a single aperture of substantially fixed dimension through patient support panel 1102 will accommodate a wide variety of breast stabilization elements e.g., 1108 having different respective diameters and other configurations and parameters, where the corresponding radial width of the second rim element 1124 serves to adapt these different dimensions to one another.

One of skill in the art will appreciate that the presence of a discrete rim element is optional, and that in certain embodiments of the invention, a single uniform material will constitute both the first body portion 1122 of the breast stabilization unit 1108 and the second rim element 1124 of the breast stabilization unit 1108 as a single integrally formed item. In still other embodiments of the invention, internal reinforcement, such as, for example, reinforcing fibers of glass, carbon, polymer, or other material, will be present in one or another region of the breast stabilization unit 1108. It will be appreciated that any transition in composition between one and another of such regions may be abrupt or gradual as deemed appropriate in relation to the requirements of a particular mode or application of the invention.

It will be understood in light of the entirety of the present disclosure that having established illustrated exemplary characteristics of the aperture and interface surface region 1132 of the patient support panel 1102, these characteristics will form a standard interface to which any of a wide variety of breast stabilization units will be prepared and coupled. Accordingly, in certain embodiments of the invention, a breast stabilization unit will be prepared having the standard interface at its upper radial periphery, and having bespoke dimensions customized according to the requirements and/or parameters (e.g., dimensions) of a particular patient, procedure, diagnostic or mode of operation. In certain embodiments, as discussed above, the breast stabilization unit will be prepared using locally available (i.e., at the imaging facility) additive or subtractive manufacturing equipment and processes.

In certain applications, the breast stabilizer unit 1108 is configured and adjusted to maintain an approximate geometric centroid of the breast coincident with intersection of an axis of rotation of a rotary gantry and a longitudinal axis of the x-ray beam 1114. It will be appreciated by one of skill in the art, however, that any of a wide variety of placements and configurations of the breast will be desirable in respect to a particular patient, application, or imaging objective, and will be achieved by an appropriate shape, configuration, and placement of the breast stabilizer unit 1108.

Accordingly, the breast stabilizer unit 1108 is arranged, adapted and configured to support, stabilize and hold in place, at least a portion of a subject breast, with respect to the transit path of an x-ray detector, during imaging of the breast by imaging system 1100.

A variety of different arrangements are well suited to maintaining the breast stabilizer unit 1108 substantially stable and immobile with respect to imaging system 1100 during imaging. For example, according to certain aspects of the invention, the breast stabilizer unit 1108 can be supported from above, from below, from a side, or in any other manner considered beneficial and/or consistent with the requirements of a particular system, application, patient or imaging modality.

These various arrangements will be employed individually and/or in combination depending on the specific requirements of a particular application, and the use of one arrangement should not be presumed to preclude the concurrent use of another arrangement or modality. Accordingly, it will be understood that the configurations discussed herewith are merely exemplary of a variety of devices and arrangements, including combinations of such devices and arrangements, that will be clear to the practitioner of ordinary skill in the art in light of the present disclosure.

Figure 12:
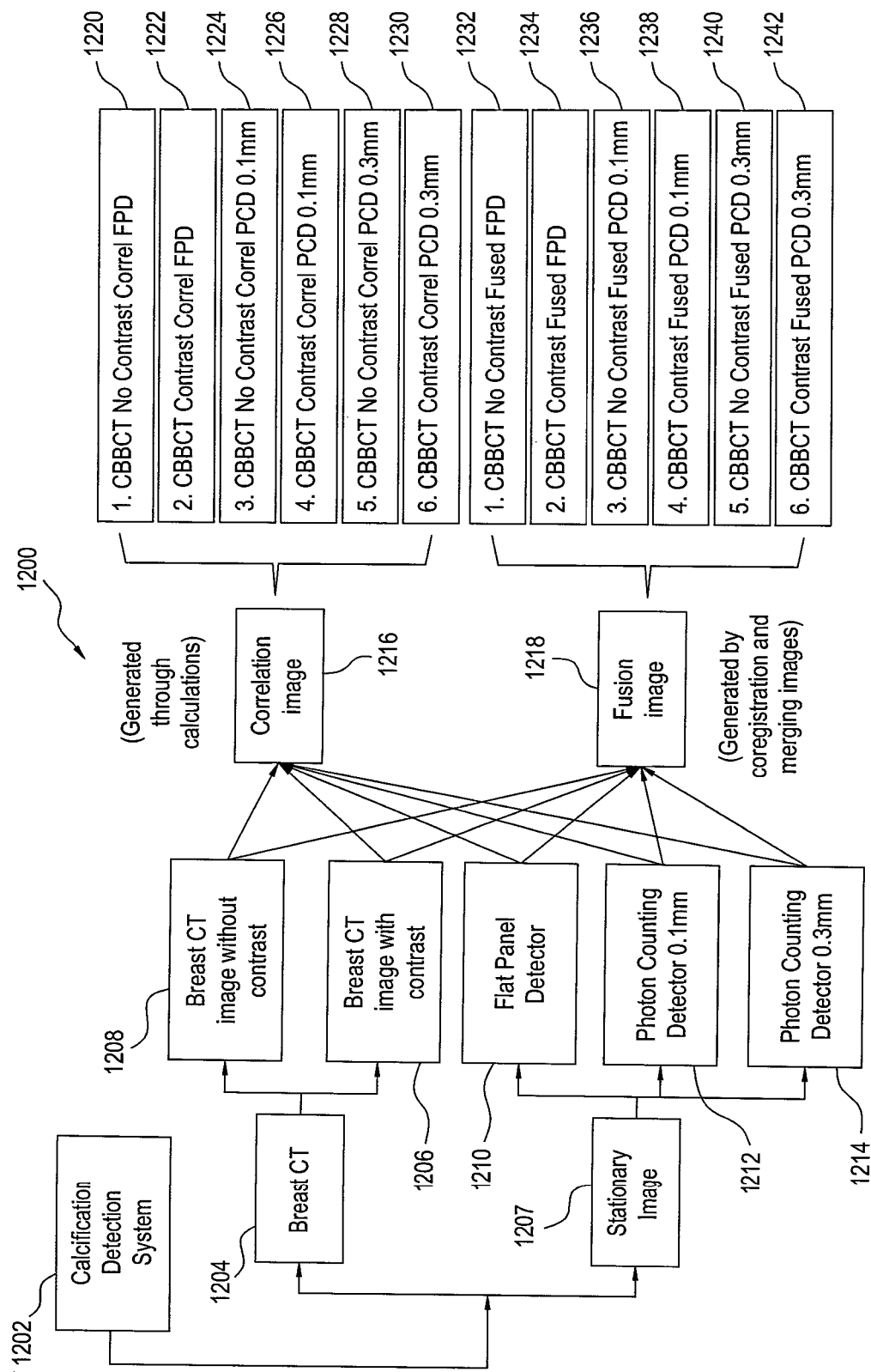
FIG. 12 shows, in schematic block diagram form, aspects of processing systems and methods employing exemplary imaging modalities according to principles of the invention.

FIG. 12 shows, in schematic block diagram form, exemplary aspects of processing systems and methods according to principles of the invention 1200, including 12 exemplary operational modalities.

Consistent with the totality of the description above, a CBBCT system 1202, including calcification detection features according to the present invention, is configured to prepare an enhanced tomographic data set for a breast CT of a subject breast. The CBBCT image produced by system 1202 is enhanced by image processing of one or more tomographic images with one or more stationary images acquired by the CBBCT system.

Accordingly, CBBCT system 1202 is configured and operated to acquire one or more CBBCT image data sets 1204. Depending on a selected mode of operation, the one or more acquired CBBCT image data sets 1204 is acquired with the use of an injected contrast agent 1206, and/or the one or more acquired CBBCT image data sets 1204 is acquired without the use of an injected contrast agent 1208.

The CBBCT system 1202 is further configured and operated to acquire one or more stationary image data sets 1207. Depending on a selected mode of operation, the one or more acquired stationary image data sets 1207 is acquired using a flat panel x-ray detector 1210; and/or the one or more acquired stationary image data sets 1207 is acquired using a photon counting x-ray detector receiving x-rays from an x-ray source configured to have a 0.1 mm focal spot 1212; and/or the one or more acquired stationary image data sets 1207 is acquired using a photon counting x-ray detector receiving x-rays from an x-ray source configured to have a 0.3 mm focal spot 1214.

A processor of the CBBCT system 1202 is configured and operated to receive the respective data sets acquired as indicated above, and to combine them through tomographic calculations to produce a correlation image 1216. In alternate modes of operation, CBBCT system, 1202 is further configured and operated to receive the respective data sets acquired as indicated above, and to combine them through co-registration and merging images to produce a fusion image 1218.

Accordingly, where a correlation image 1216 is produced, such a correlation image will be produced in one or more of the following modalities:
1. CBBCT image without contrast correlated with a flat panel detector stationary image 1220.
2. CBBCT image with contrast correlated with a flat panel detector stationary image 1222.
3. CBBCT image without contrast correlated with a photon counting detector stationary image and a 0.1 mm focal spot size 1224.
4. CBBCT image with contrast correlated with a photon counting detector stationary image and a 0.1 mm focal spot size 1226.
5. CBBCT image without contrast correlated with a photon counting detector stationary image and a 0.3 mm focal spot size 1228.
6. CBBCT image with contrast correlated with a photon counting detector stationary image and a 0.3 mm focal spot size of 1230.

Accordingly, where a fusion image 1218 is produced, such a fusion image will be produced in one or more of the following modalities:
1. CBBCT image without contrast fused with a flat panel detector stationary image 1232.

2. CBBCT image with contrast fused with a flat panel detector stationary image 1234.
3. CBBCT image without contrast fused with a photon counting detector stationary image and a 0.1 mm focal spot size 1236.
4. CBBCT image with contrast fused with a photon counting detector stationary image and a 0.1 mm focal spot size 1238.
5. CBBCT image without contrast fused with a photon counting detector stationary image and a 0.3 mm focal spot size 1240.
6. CBBCT image with contrast fused with a photon counting detector stationary image and a 0.3 mm focal spot size 1242.

In view of the disclosure associated with FIG. 12 and, more broadly, in view of the totality of the present disclosure, one of skill in the art will readily appreciate that the image acquisition and processing methods and modalities presented herewith are merely exemplary of a much larger set of methods and modalities. These novel methods and modalities, while surprising and effective, become clear to the practitioner of ordinary skill in the art once having been exposed to the present disclosure. Accordingly, while an extensive listing of all possible methods and modalities exceeds the reasonable scope of the present document, it should be understood that this document is intended to disclose the entirety of the methods, systems and apparatus, structure, methods and results that would become apparent to the skilled practitioner in possession of the present disclosure.

In certain embodiments, the invention includes a method of imaging a breast calcification in vitro including disposing a patient on a CBBCT imaging system and supporting the patient to minimize motion of the breast. Thereafter, the method includes rotating a gantry of the CBBCT imaging system to produce rotation of an x-ray source.

The method also includes repetitively projecting a first x-ray beam from the x-ray source and repetitively passing a portion of the first x-ray beam through the breast and repetitively detecting the first x-ray beam with a flat panel detector to capture a first plurality of image data sets.

In addition, the method includes processing data of the first plurality of image data sets to produce a first CBBCT imaging model as well as evaluating the first CBBCT imaging model to identify a region of interest likely to contain the breast calcification. The method further includes aligning the CBBCT imaging system with the region of interest and holding the CBBCT imaging system stationary for a stationary image acquisition cycle as well as projecting a second x-ray beam from an x-ray source.

In further aspects, the method includes passing the second x-ray beam through a region of the breast and detecting the second x-ray beam with an x-ray detector to capture a stationary image data set as well as processing data of the first plurality of image data sets with the stationary image data set to produce an improved CBBCT imaging model resolving the calcification.

In some embodiments the invention includes imaging a breast calcification in vitro by passing the second x-ray beam through a shielding collimator to narrow the second x-ray beam to target the region of interest. In certain embodiments processing the data of the first plurality of image data sets with the stationary image data set includes processing the first plurality of image data sets with the stationary image data set to produce an improved CBBCT imaging model.

According to certain embodiment of the invention the processing the data of the first plurality of image data sets with the stationary image data set includes processing the first CBBCT imaging model with the stationary image data set to produce an improved CBBCT imaging model. Also, in certain embodiments of the invention, supporting the patient to minimize motion of the includes supporting a breast of the patient with a breast stabilization unit.

According to some aspects of the invention, the CBBCT system includes a sensor. The sensor may optionally be disposed in a breast stabilization unit. The sensor may be used to sense a heartbeat of the patient. In other embodiments of the invention, the sensor may be used to sense respiration of the patient.

Further embodiments of the invention include synchronizing detection of the first x-ray beam with a heartbeat of the patient. Other embodiments of the invention include synchronizing detection of the second x-ray beam with a heartbeat of the patient.

In certain embodiments of the invention, the first x-ray beam is produced from a 0.3 mm focal spot. In certain embodiments of the invention, the second x-ray beam is produced from a 0.1 mm focal spot. Sometimes, a single x-ray source is configured to produce both the firstx-ray beam and the second x-ray beam. Detection of the second x-ray beam will be done with a photon counting detector in certain embodiments of the invention. According to certain embodiments of the invention, the data produced will be evaluated with an artificial intelligence deep learning process.

In certain embodiments of the invention, the data of the first plurality of image data sets is combined with the stationary image data set to prepare a calculated correlation image. In other embodiments of the invention, the data of the first plurality of image data sets is combined with the stationary image data set to prepare a co-registered fusion image.

In certain embodiments of the invention, the gantry is repetitively arrested during a rotation to allow images to be captured between gantry motions. According to certain embodiment of the invention, the gantry is rotated through an arc of 1800 plus an arc width of the flat panel detector during image acquisition.

While the exemplary embodiments described above have been chosen primarily from the field of breast calcification detection, one of skill in the art will appreciate that the principles of the invention are equally well applied, and that the benefits of the present invention are equally well realized in a wide variety of other imaging systems and applications.

Further, while the invention has been described in detail in connection with the presently preferred embodiments, it should be understood that the invention is not limited to such disclosed embodiments. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description, but is only limited by the scope of the appended claims.

The invention claimed is:

1. A method of imaging a breast calcification in vitro comprising:
    disposing a patient on a CBBCT imaging system;
    supporting said patient to minimize a motion of said breast;
    rotating a gantry of said CBBCT imaging system to produce rotation of an x-ray source;

repetitively projecting a first x-ray beam from said x-ray source;
repetitively passing a portion of said first x-ray beam through said breast;
repetitively detecting said first x-ray beam with a flat panel detector to capture a first plurality of image data sets;
processing data of said first plurality of image data sets to produce a first CBBCT imaging model;
evaluating said first CBBCT imaging model to identify a region of interest likely to contain said breast calcification;
aligning said CBBCT imaging system with said region of interest;
holding said CBBCT imaging system stationary for a stationary image acquisition cycle;
projecting a second x-ray beam from an x-ray source;
passing said second x-ray beam through a region of said breast;
detecting said second x-ray beam with an x-ray detector to capture a stationary image data set;
processing data of said first plurality of image data sets with said stationary image data set to produce an improved CBBCT imaging model resolving said calcification.

2. A method of imaging a breast calcification in vitro as defined in claim 1 comprising:
passing said second x-ray beam through a shielding collimator to narrow said second x-ray beam to target said region of interest.

3. A method of imaging a breast calcification in vitro as defined in claim 1 wherein said processing said data of said first plurality of image data sets with said stationary image data set comprises:
processing said first plurality of image data sets with said stationary image data set to produce an improved CBBCT imaging model.

4. A method of imaging a breast calcification in vitro as defined in claim 1 wherein said processing said data of said first plurality of image data sets with said stationary image data set comprises:
processing said first CBBCT imaging model with said stationary image data set to produce an improved CBBCT imaging model.

5. A method of imaging a breast calcification in vitro as defined in claim 1 wherein said supporting said patient to minimize motion of said breast comprises:
supporting a breast of said patient with a breast stabilization unit.

6. A method of imaging a breast calcification in vitro as defined in claim 1 wherein said CBBCT imaging system comprises:
a sensor.

7. A method of imaging a breast calcification in vitro as defined in claim 6 wherein said sensor is disposed within a breast stabilization unit.

8. A method of imaging a breast calcification in vitro as defined in claim 6, further comprising:
sensing a heartbeat of said patient.

9. A method of imaging a breast calcification in vitro as defined in claim 6, further comprising:
sensing respiration of said patient.

10. A method of imaging a breast calcification in vitro as defined in claim 6, further comprising:
synchronizing said detecting said first x-ray beam with a heartbeat of said patient.

11. A method of imaging a breast calcification in vitro as defined in claim 6, further comprising:
synchronizing said detecting said second x-ray beam with a heartbeat of said patient.

12. A method of imaging a breast calcification in vitro as defined in claim 1 wherein said repetitively projecting said first x-ray beam from an x-ray source comprises:
repetitively projecting a first x-ray beam from a 0.3 mm focal spot.

13. A method of imaging a breast calcification in vitro as defined in claim 1 wherein said projecting said second x-ray beam from an x-ray source comprises:
projecting said second x-ray beam from a 0.1 mm focal spot.

14. A method of imaging a breast calcification in vitro as defined in claim 1 wherein said first x-ray beam and said second x-ray beam are projected from a common x-ray source.

15. A method of imaging a breast calcification in vitro as defined in claim 1 wherein detecting said second x-ray beam with an x-ray detector comprises:
detecting said second x-ray beam with a photon counting x-ray detector.

16. A method of imaging a breast calcification in vitro as defined in claim 1 wherein said evaluating said first CBBCT imaging model to identify a region of interest comprises:
evaluating said first CBBCT imaging model with an artificial intelligence deep learning process.

17. A method of imaging a breast calcification in vitro as defined in claim 1 wherein said processing said data of said first plurality of image data sets with said stationary image data set comprises:
preparing a calculated correlation image.

18. A method of imaging a breast calcification in vitro as defined in claim 1 wherein said processing said data of said first plurality of image data sets with said stationary image data set comprises:
preparing a co-registered fusion image.

19. A method of imaging a breast calcification in vitro as defined in claim 1 comprising:
repetitively arresting said rotation of said x-ray source by repetitively arresting said gantry between repetitively projecting a first x-ray beam from said x-ray source.

20. A method of imaging a breast calcification in vitro as defined in claim 1 wherein said rotating said gantry of said CBBCT imaging system to produce rotation of an x-ray source comprises:
rotating said gantry through an arc of 180° plus an arc width of said flat panel detector.

* * * * *